United States Patent
Keidar et al.

(10) Patent No.: US 10,624,743 B2
(45) Date of Patent: Apr. 21, 2020

(54) BEATING-HEART MITRAL VALVE CHORDAE REPLACEMENT

(71) Applicant: Edwards Lifesciences Corporation, Irvine, CA (US)

(72) Inventors: Yaron Keidar, Irvine, CA (US); Adam J. Yestrepsky, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 89 days.

(21) Appl. No.: 15/491,809

(22) Filed: Apr. 19, 2017

(65) Prior Publication Data
US 2017/0304050 A1 Oct. 26, 2017

Related U.S. Application Data

(60) Provisional application No. 62/326,609, filed on Apr. 22, 2016.

(51) Int. Cl.
*A61F 2/24* (2006.01)
*A61B 17/30* (2006.01)
(Continued)

(52) U.S. Cl.
CPC ........ *A61F 2/2457* (2013.01); *A61B 17/0401* (2013.01); *A61B 17/30* (2013.01);
(Continued)

(58) Field of Classification Search
CPC ........ A61B 17/0401; A61B 2017/0406; A61B 2017/308; A61B 2017/0409; A61B 2017/00243; A61B 2017/048; A61F 2/2457; A61F 2/2466; A61F 2/24; A61F 2/2442; A61F 2/2451; A61F 2/246; A61F 2/2463; A61F 2/2454
See application file for complete search history.

(56) References Cited

U.S. PATENT DOCUMENTS 3,752,516 A 8/1973 Mumma
4,403,797 A 9/1983 Ragland, Jr.
(Continued)

FOREIGN PATENT DOCUMENTS

EP 0791330 A3 11/1997
WO 2008013869 A2 1/2008
(Continued)

OTHER PUBLICATIONS

Alfieri, O. el al., "The double-orifice technique in mitral valve repair: a simple solution for complex problems," (2001) J. Thorac. Cardiovasc. Surg., 122(4):674-681.
(Continued)

*Primary Examiner* — Katrina M Stransky
*Assistant Examiner* — Brigid K Byrd
(74) *Attorney, Agent, or Firm* — Hale & Chang

(57) ABSTRACT

Methods and devices for the treatment of cardiac valve dysfunction through the placement of lines and anchors. The lines and anchors can form artificial chordae between valve leaflets and the ventricular wall or papillary muscles or connect the two valve leaflets together. The methods and devices offer a mechanism for performing this technique with the heart still beating, and allows for the placement of multiple lines with a single device.

7 Claims, 21 Drawing Sheets

(51) Int. Cl.
*A61B 17/04* (2006.01)
A61B 17/00 (2006.01)
(52) U.S. Cl.
CPC .. *A61F 2/2466* (2013.01); *A61B 2017/00243* (2013.01); *A61B 2017/0406* (2013.01); *A61B 2017/0409* (2013.01); *A61B 2017/0464* (2013.01); *A61B 2017/308* (2013.01)

(56) References Cited

U.S. PATENT DOCUMENTS

| | | |
|---|---|---|
| 4,662,376 A | 5/1987 | Belanger |
| 4,807,625 A | 2/1989 | Singleton |
| 5,144,961 A | 9/1992 | Chen et al. |
| 5,147,316 A | 9/1992 | Castillenti |
| 5,312,423 A | 5/1994 | Rosenbluth et al. |
| 5,391,176 A | 2/1995 | de la Torre |
| 5,405,352 A | 4/1995 | Weston |
| 5,454,821 A | 10/1995 | Harm et al. |
| 5,472,446 A | 12/1995 | de la Torre |
| 5,507,754 A | 4/1996 | Green et al. |
| 5,527,323 A | 6/1996 | Jervis et al. |
| 5,554,184 A | 9/1996 | Machiraju |
| 5,626,614 A | 5/1997 | Hart |
| 5,643,293 A | 7/1997 | Kogasaka et al. |
| 5,681,331 A | 10/1997 | de la Torre et al. |
| 5,716,368 A | 2/1998 | de la Torre et al. |
| 5,727,569 A | 3/1998 | Benetti et al. |
| 5,728,109 A | 3/1998 | Schulze et al. |
| 5,746,752 A | 5/1998 | Burkhart |
| 5,769,862 A | 6/1998 | Kammerer et al. |
| 5,797,928 A | 8/1998 | Kogasaka |
| 5,824,065 A | 10/1998 | Gross |
| 5,931,868 A | 8/1999 | Gross |
| 5,957,936 A | 9/1999 | Yoon et al. |
| 5,971,447 A | 10/1999 | Steck, III |
| 6,010,531 A | 1/2000 | Donlon et al. |
| 6,074,417 A | 6/2000 | Peredo |
| 6,269,819 B1 | 8/2001 | Oz et al. |
| 6,332,893 B1 | 12/2001 | Mortier et al. |
| 6,562,051 B1 | 5/2003 | Bolduc et al. |
| 6,626,930 B1 | 9/2003 | Allen et al. |
| 6,629,534 B1 | 10/2003 | St. Goar et al. |
| 6,840,246 B2 | 1/2005 | Downing |
| 6,921,408 B2 | 7/2005 | Sauer |
| 6,978,176 B2 | 12/2005 | Lattouf |
| 6,991,635 B2 | 1/2006 | Takamoto et al. |
| 6,997,950 B2 | 2/2006 | Chawla |
| 7,112,207 B2 | 9/2006 | Allen et al. |
| 7,291,168 B2 | 11/2007 | Macoviak et al. |
| 7,294,148 B2 | 11/2007 | McCarthy |
| 7,309,086 B2 | 12/2007 | Carrier |
| 7,316,706 B2 | 1/2008 | Bloom et al. |
| 7,373,207 B2 | 5/2008 | Lattouf |
| 7,431,692 B2 | 10/2008 | Zollinger et al. |
| 7,513,908 B2 | 4/2009 | Lattouf |
| 7,534,260 B2 | 5/2009 | Lattouf |
| 7,608,091 B2 | 10/2009 | Goldfarb et al. |
| 7,618,449 B2 | 11/2009 | Tremulis et al. |
| 7,632,308 B2 | 12/2009 | Loulmet |
| 7,635,386 B1 | 12/2009 | Gammie |
| 7,666,196 B1 | 2/2010 | Miles |
| 7,744,609 B2 | 6/2010 | Allen et al. |
| 7,837,727 B2 | 11/2010 | Goetz et al. |
| 7,871,368 B2 | 1/2011 | Zollinger et al. |
| 7,871,433 B2 | 1/2011 | Lattouf |
| 7,959,650 B2 | 6/2011 | Kaiser et al. |
| 8,029,518 B2 | 10/2011 | Goldfarb et al. |
| 8,029,565 B2 | 10/2011 | Lattouf |
| 8,043,368 B2 | 10/2011 | Crabtree |
| 8,147,542 B2 | 4/2012 | Maisano et al. |
| 8,226,711 B2 | 7/2012 | Mortier et al. |
| 8,241,304 B2 | 8/2012 | Bachman |
| 8,252,050 B2 | 8/2012 | Maisano et al. |
| 8,292,884 B2 | 10/2012 | Levine et al. |
| 8,303,622 B2 | 11/2012 | Alkhatib |
| 8,333,788 B2 | 12/2012 | Maiorino |
| 8,382,829 B1 | 2/2013 | Call et al. |
| 8,439,969 B2 | 5/2013 | Gillinov et al. |
| 8,454,656 B2 | 6/2013 | Tuval |
| 8,465,500 B2 | 6/2013 | Speziali |
| 8,475,525 B2 | 7/2013 | Maisano et al. |
| 8,500,800 B2 | 8/2013 | Maisano et al. |
| 8,608,758 B2 | 12/2013 | Singhatat et al. |
| 8,663,278 B2 | 3/2014 | Mabuchi et al. |
| 8,771,296 B2 | 7/2014 | Nobles et al. |
| 8,828,053 B2 | 9/2014 | Sengun et al. |
| 8,852,213 B2 | 10/2014 | Gammie et al. |
| 8,940,008 B2 | 1/2015 | Kunis |
| 9,131,884 B2 | 9/2015 | Holmes et al. |
| 9,192,287 B2 | 11/2015 | Saadat et al. |
| 2002/0013571 A1 | 1/2002 | Goldfarb et al. |
| 2003/0023254 A1 | 1/2003 | Chiu |
| 2003/0094180 A1 | 5/2003 | Benetti |
| 2003/0105519 A1 | 6/2003 | Fasol et al. |
| 2003/0120264 A1 | 6/2003 | Lattouf |
| 2003/0120341 A1 | 6/2003 | Shennib et al. |
| 2004/0044365 A1 | 3/2004 | Bachman |
| 2004/0093023 A1 | 5/2004 | Allen et al. |
| 2004/0143323 A1 | 7/2004 | Chawla |
| 2004/0172046 A1* | 9/2004 | Hlavka ............ A61B 17/00234 606/142 |
| 2004/0199183 A1 | 10/2004 | Oz et al. |
| 2005/0004667 A1 | 1/2005 | Swinford et al. |
| 2005/0075654 A1 | 4/2005 | Kelleher |
| 2005/0149067 A1 | 7/2005 | Takemoto et al. |
| 2005/0149093 A1 | 7/2005 | Pokorney |
| 2005/0154402 A1 | 7/2005 | Sauer et al. |
| 2005/0216036 A1 | 9/2005 | Nakao |
| 2005/0216077 A1 | 9/2005 | Mathis et al. |
| 2005/0261710 A1 | 11/2005 | Sakamoto et al. |
| 2005/0267493 A1 | 12/2005 | Schreck et al. |
| 2006/0100698 A1 | 5/2006 | Lattouf |
| 2006/0111739 A1 | 5/2006 | Staufer et al. |
| 2006/0167541 A1 | 7/2006 | Lattouf |
| 2006/0190030 A1 | 8/2006 | To et al. |
| 2006/0282088 A1 | 12/2006 | Ryan |
| 2007/0001857 A1 | 1/2007 | Hartmann et al. |
| 2007/0049952 A1 | 3/2007 | Weiss |
| 2007/0055292 A1 | 3/2007 | Ortiz et al. |
| 2007/0112422 A1 | 5/2007 | Dehdashtian |
| 2007/0118151 A1* | 5/2007 | Davidson ........ A61B 17/00234 606/144 |
| 2007/0118154 A1 | 5/2007 | Crabtree |
| 2007/0149995 A1 | 6/2007 | Quinn et al. |
| 2007/0197858 A1 | 8/2007 | Goldfarb et al. |
| 2007/0213582 A1 | 9/2007 | Zollinger et al. |
| 2007/0270793 A1 | 11/2007 | Lattouf |
| 2008/0004597 A1 | 1/2008 | Lattouf et al. |
| 2008/0009888 A1 | 1/2008 | Ewers et al. |
| 2008/0065203 A1 | 3/2008 | Khalapyan |
| 2008/0140093 A1 | 6/2008 | Stone et al. |
| 2008/0167714 A1 | 7/2008 | St. Goar et al. |
| 2008/0188893 A1 | 8/2008 | Selvitelli et al. |
| 2008/0228223 A1 | 9/2008 | Alkhatib |
| 2008/0249504 A1 | 10/2008 | Lattouf et al. |
| 2008/0269781 A1 | 10/2008 | Funamura et al. |
| 2009/0005863 A1 | 1/2009 | Goetz et al. |
| 2009/0043153 A1 | 2/2009 | Zollinger et al. |
| 2009/0088837 A1* | 4/2009 | Gillinov ............... A61B 5/1072 623/2.1 |
| 2009/0105729 A1 | 4/2009 | Zentgraf |
| 2009/0105751 A1 | 4/2009 | Zentgraf |
| 2009/0270789 A1* | 10/2009 | Maxymiv ........ A61B 17/00234 604/22 |
| 2009/0276038 A1 | 11/2009 | Tremulis et al. |
| 2010/0023117 A1 | 1/2010 | Yoganathan et al. |
| 2010/0023118 A1 | 1/2010 | Medlock et al. |
| 2010/0042147 A1 | 2/2010 | Janovsky et al. |
| 2010/0160719 A1* | 6/2010 | Kassab ............ A61M 25/0147 600/37 |
| 2010/0174297 A1 | 7/2010 | Speziali |
| 2010/0179574 A1 | 7/2010 | Longoria et al. |
| 2010/0210899 A1 | 8/2010 | Schankereli |

(56) References Cited

U.S. PATENT DOCUMENTS

| | | | |
|---|---|---|---|
| 2010/0298930 A1 | 11/2010 | Orlov | |
| 2011/0015476 A1 | 1/2011 | Franco | |
| 2011/0022083 A1 | 1/2011 | DiMatteo et al. | |
| 2011/0022084 A1 | 1/2011 | Sengun et al. | |
| 2011/0028995 A1 | 2/2011 | Miraki et al. | |
| 2011/0029071 A1 | 2/2011 | Zlotnick et al. | |
| 2011/0060407 A1 | 3/2011 | Ketai et al. | |
| 2011/0106106 A1 | 5/2011 | Meier et al. | |
| 2011/0144743 A1 | 6/2011 | Lattouf | |
| 2011/0264072 A1* | 10/2011 | Kunis | A61B 17/3478 604/506 |
| 2011/0264208 A1 | 10/2011 | Duffy et al. | |
| 2011/0270278 A1 | 11/2011 | Overes et al. | |
| 2011/0288637 A1 | 11/2011 | De Marchena | |
| 2011/0307055 A1 | 12/2011 | Goldfarb et al. | |
| 2012/0004669 A1 | 1/2012 | Overes et al. | |
| 2012/0059394 A1* | 3/2012 | Brenner | A61B 1/00087 606/142 |
| 2012/0143215 A1 | 6/2012 | Corrao et al. | |
| 2012/0150223 A1 | 6/2012 | Manos et al. | |
| 2012/0179184 A1 | 7/2012 | Orlov | |
| 2012/0184971 A1 | 7/2012 | Zentgraf et al. | |
| 2012/0203072 A1 | 8/2012 | Lattouf et al. | |
| 2012/0226294 A1 | 9/2012 | Tuval | |
| 2012/0226349 A1 | 9/2012 | Tuval et al. | |
| 2013/0018459 A1 | 1/2013 | Maisano et al. | |
| 2013/0035757 A1 | 2/2013 | Zentgraf et al. | |
| 2013/0253641 A1 | 9/2013 | Lattouf | |
| 2013/0282059 A1 | 10/2013 | Ketai et al. | |
| 2013/0345749 A1 | 12/2013 | Sullivan et al. | |
| 2014/0031926 A1 | 1/2014 | Kudlik et al. | |
| 2014/0039607 A1 | 2/2014 | Kovach | |
| 2014/0067052 A1 | 3/2014 | Chau et al. | |
| 2014/0114404 A1 | 4/2014 | Gammie et al. | |
| 2014/0214152 A1 | 7/2014 | Bielefeld | |
| 2014/0243968 A1 | 8/2014 | Padala | |
| 2014/0364938 A1 | 12/2014 | Longoria et al. | |
| 2015/0032127 A1 | 1/2015 | Gammie et al. | |
| 2015/0045879 A1 | 2/2015 | Longoria et al. | |
| 2018/0235758 A1* | 8/2018 | Biadillah | A61F 2/2463 |

FOREIGN PATENT DOCUMENTS

| | | |
|---|---|---|
| WO | 2007100268 A3 | 10/2008 |
| WO | 2008124110 A3 | 12/2008 |
| WO | 2008143740 A3 | 2/2009 |
| WO | 2006078694 A3 | 4/2009 |
| WO | 2009081396 A2 | 7/2009 |
| WO | 2010070649 A1 | 6/2010 |
| WO | 2010105046 A1 | 9/2010 |
| WO | 2012137208 A1 | 10/2012 |
| WO | 2013003228 A1 | 1/2013 |
| WO | 2014093861 A1 | 6/2014 |
| WO | 2015020816 A1 | 2/2015 |

OTHER PUBLICATIONS

Barbero-Marcial, M. et al., "Transxiphoid Approach Without Median Sternotomy for the Repair of Atrial Septa! Defects," (1998) Ann. Thorne. Surg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitra! valve repair by replacement of chordae tendineae with polytetrafluoroethylene sutures," (1991) J. Thorne. Cardiovasc. Surg., 101 (3):495-50 I.

David, T. E. et al., "Replacement of chordae tendineae with Gore-Tex sutures: a ten-year experience," (1996) J. Heart Valve Dis., 5(4):352-355.

Doty, D. B. et al., "Full-Spectrum Cardiac Surgery Through a Minimal Incision: Mini-Sternotomy (Lower Half) Technique," ( 1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitrnl valve prolapse," (1997) J. Heal1 Valve Dis., 6(6):594-598.

Frater, R. W. M. ct al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thome. Surg., 75:809-811.

Kasegawa, H. ct al., "Simple method for detennining proper length of al1ificial chordae in mitral valve repair," ( 1994) Ann. Thome. Surg., 57(1 ):237-239.

Kobayashj, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thome. Cardiovasc. Surg., 133( I): 247-249.

Maisano, F. et al., "The double-orifice technique as a standardized approach to treat mitral regurgitation due to severe myxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posteromedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *I!Niversity of Maryland, Baltimore*, Case No. IPR2016-00208, Petition for inter PartesReview of U.S. Pat. No. 7,635,386, dated Nov. 18, 2015, 65 pages.

*Neochord, Inc.* v. *University of Maryland, Bal Tim Ore*, Case No. JPR2016-00208, Decision on Institution of Inter Faries Review,37 CFR §42. I 08, Paper 6, Entered May 24, 2016, 28 pages.

*Neochord, Inc.* v. *University of Maryland, Baltimore*, Case No. IPR2016-00208, Declaration of Dr. Lishan Aklog, dated Nov. 17, 2015, 91 pages.

Nigro, J. J. et al., "Neochordal repair of the posterior mitral leaflet," (2004) J. Thorne. Cardiovasc. Surg., 127 (2):440-447.

Phillips, M. R. et al., "Repair of anterior leaflet mitral valve prolapse: chordal replacement versus chordal shrntening," (2000) Ann. Thorac. Surg., 69(1 ):5-29.

Russo, M. J. ct al. •Transapical Approach for Mitra! Valve Repair during Insertion of a Left Ventricular Assist Device, Hindawi Publishing Corporation, The Scientific World Journal, V olumc 2013, Article ID 925310, [ online], Retrieved from the internet: <URL: http://dx.doi.org/J 0.1155/2013/92531 0> Apr. 11, 2013, 4 pages.

Sarsam, M.A. I., "Simplified technique for determining the length of artificial cl1ordae in mitral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database, .. (2003) Ann. Thorne. Surg., 75:820-825.

(56) References Cited

OTHER PUBLICATIONS

Speziali, G. et al., "Coll'ection of Mitral Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heaii surgery without cardiopulmonary bypass: Atrial septal defect closure in a swine model," (2005) J. Thorne. Cardiovasc. Surg., 130: 1348-1357.

Von Oppell, U. O. et al., "Chordal replacement for both minimally invasive and conventional mitral valve surgery using premeasured Gore-Tex loops," (2000) Ann. Thorne. Surg., 70(6):2166-2168.

Zussa. C. et al., Artificial mitral valve chordae: experimental and clinical experience;• ( 1990) Ann. Thorne. Surg., 50 (3):367-373.

Zussa, C. et al., "Seven-year experience with chordal replacement with expanded polytetrafluoroethylene in floppy mitral valve," (1994)1. Thorac. Cardiovasc. Surg., 108(1):37-41.

Zussa, C. et al., "Surgical technique for artificial mitral chordae implantation," ( 1991) Journal of Cardiac Surgery, 6 (4):432-438.

Zussa, C., "Artificial chordae," (1995) J. Heart Valve Dis., 4(2):S249-S256.

\* cited by examiner

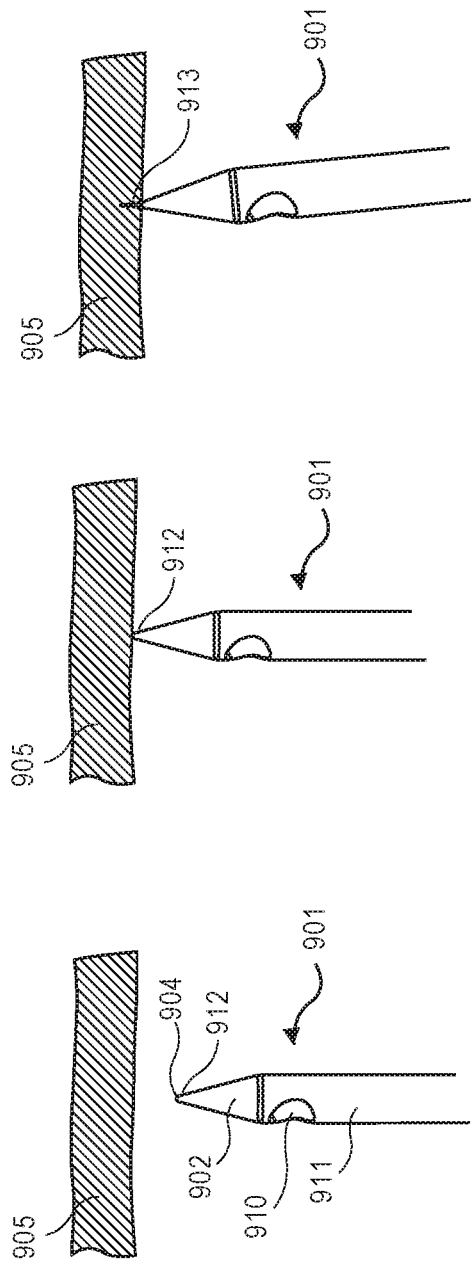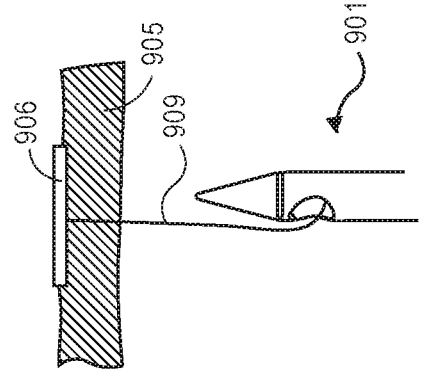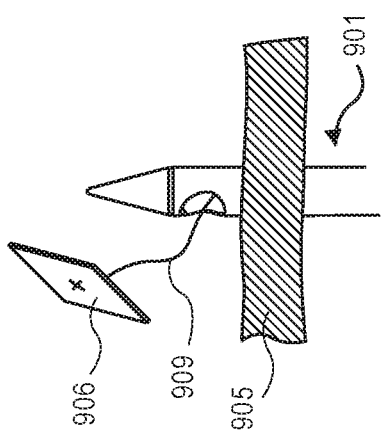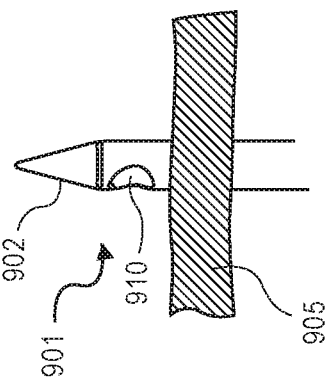

BEATING-HEART MITRAL VALVE CHORDAE REPLACEMENT

RELATED APPLICATIONS

This application claims the benefit of U.S. Application Ser. No. 62/326,609, filed on Apr. 22, 2016, entitled "Catheter With a Collapsible Funnel-Shaped Suction Cup for Placing Prosthetic Chords for a Heart Valve," the disclosure of which is incorporated herein by reference in its entirety.

FIELD OF THE INVENTION

The various embodiments relate to treatment of mitral valve dysfunction through the placement of artificial chordae between the leaflets and the ventricular wall or papillary muscles in general, and more particularly to replacing the chordae with sutures and pledgets threaded thereon, and further to approximating opposing leaflets together.

BACKGROUND INFORMATION

1. Field of the Disclosure

The disclosure herein relates to methods and devices for treating mitral valve dysfunction through the placement of artificial chordae between the leaflets and the ventricular wall or papillary muscles, while the heart is still beating. The disclosure herein further relates to the placement of multiple artificial chordae with a single device, and the approximation of leaflets.

2. Description of the Background

As illustrated in FIG. 1, the human heart 10 has four chambers, which include two upper chambers denoted as atria 12, 16 and two lower chambers denoted as ventricles 14, 18. A septum 20 divides the heart 10 and separates the left atrium 12 and left ventricle 14 from the right atrium 16 and right ventricle 18. The heart further contains four valves 22, 24, 26, and 28. The valves function to maintain the pressure and unidirectional flow of blood through the body and to prevent blood from leaking back into a chamber from which it has been pumped.

Two valves separate the atria 12, 16 from the ventricles 14, 18, denoted as atrioventricular valves. The left atrioventricular valve, the mitral valve 22, controls the passage of oxygenated blood from the left atrium 12 to the left ventricle 14. A second valve, the aortic valve 24, separates the left ventricle 14 from the aortic artery (aorta) 30, which delivers oxygenated blood via the circulation to the entire body. The aortic valve 24 and mitral valve 22 are part of the "left" heart, which controls the flow of oxygen-rich blood from the lungs to the body. The right atrioventricular valve, the tricuspid valve 26, controls passage of deoxygenated blood into the right ventricle 18. A fourth valve, the pulmonary valve 28, separates the right ventricle 18 from the pulmonary trunk 32. The right ventricle 18 pumps deoxygenated blood through the pulmonary trunk 32 and arteries to the lungs wherein the blood is oxygenated and then delivered to the left atrium 12 via the pulmonary veins. Accordingly, the tricuspid valve 26 and pulmonary valve 28 are part of the "right" heart, which control the flow of oxygen-depleted blood from the body to the lungs.

Both the left and right ventricles 14, 18 constitute "pumping" chambers. The aortic valve 24 and pulmonary valve 28 lie between a pumping chamber (ventricle) and a major artery and control the flow of blood out of the ventricles and into the circulation. The aortic valve 24 and pulmonary valve 28 have three cusps, or leaflets, that open and close and thereby function to prevent blood from leaking back into the ventricles after being ejected into the lungs or aorta 30 for circulation.

Both the left and right atria 12, 16 are "receiving" chambers. The mitral valve 22 and tricuspid valve 26, therefore, lie between a receiving chamber (atrium) and a ventricle so as to control the flow of blood from the atria to the ventricles and prevent blood from leaking back into the atrium during ejection out of the ventricle. Both the mitral valve 22 and tricuspid valve 26 include two or more cusps, or leaflets (shown in FIG. 3), that are encircled by a variably dense fibrous ring of tissues known as the annulus. The valves are anchored to the walls of the ventricles by chordae tendineae (chordae) 42. The chordae tendineae 42 are cord-like tendons that connect the papillary muscles 44 to the leaflets of the mitral valve 22 and tricuspid valve 26 of the heart 10. The papillary muscles 44 are located at the base of the chordae 42 and are within the walls of the ventricles. They serve to limit the movements of the mitral valve 22 and tricuspid valve 26 and prevent them from inverting. The papillary muscles 44 do not open or close the valves of the heart, which close passively in response to pressure gradients; rather, the papillary muscles 44 brace the valves against the high pressure needed to circulate the blood throughout the body. Together, the papillary muscles 44 and the chordae tendineae 42 are known as the subvalvular apparatus. The function of the subvalvular apparatus is to keep the valves from prolapsing into the atria when they close.

The tricuspid valve 26 in FIG. 1 typically is made up of three leaflets with three papillary muscles. However, the number of leaflets can range between two and four. The three leaflets of the tricuspid valve 26 are referred to as the anterior, posterior, and septal leaflets. Although both the aortic and pulmonary valves each have three leaflets (or cusps), they do not have chordae tendineae. The mitral valve 22 has two papillary muscles 44, the anteromedial and the posterolateral papillary muscles, which attach the leaflets 52, 54 to the walls of the left ventricle 14 via the chordae tendineae 42.

FIG. 2 is an illustration of a cutaway anterior view of the "left heart" 200 in systole, as indicated by the contracted ventricular wall 201. Illustrated in FIG. 2 is the mitral valve 22 having a posterior leaflet 203 and an anterior leaflet 204, the mitral valve in a closed position. Also visible is the aortic valve 24 which is an open configuration during systole, and permits bloodflow from the left ventricle 14 to the aorta 30. During systole, when a healthy mitral valve is closed, blood does not flow from the left atrium 12 to the left ventricle 14.

As illustrated with reference to FIG. 3, a top view of a healthy mitral valve 22, the mitral valve 22 includes two leaflets, the anterior leaflet 204 and the posterior leaflet 203, and a diaphanous incomplete ring around the valve, called the annulus 205. The vast majority of patients undergoing valve surgery, such as mitral valve surgery, suffer from a degenerative disease that causes a malfunction in a leaflet of the valve, which results in prolapse and regurgitation.

One possible malfunction of a heart valve, valve regurgitation, occurs when the leaflets of the valve do not close completely thereby causing blood to leak back into the prior chamber. This type of valve malfunction typically occurs with the mitral valve and tricuspid valve.

There are three mechanisms by which a valve becomes regurgitant or incompetent; they include Carpentier's type I, type II and type III malfunctions. A Carpentier type I malfunction involves the dilation of the annulus such that normally functioning leaflets are distracted from each other and fail to form a tight seal (e.g., do not coapt properly). Included in a type I mechanism malfunction are perforations of the valve leaflets, as in endocarditis. A Carpentier's type II malfunction involves prolapse of one or both leaflets above the plane of coaptation. This is the most common cause of mitral regurgitation, and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (IIIa) or dilation of the ventricle (IIIb).

FIG. 4 illustrates a prolapsed mitral valve 22. Here, even when in systole, when the anterior 204 and posterior 203 leaflets should be in contact with each other, gap 208 remains between the two. Because one or more of the leaflets 203, 204 malfunction, the prolapsed mitral valve 22 does not close properly, and, therefore, the leaflets fail to coapt. This failure to coapt causes a gap 208 between the leaflets 203, 204 that allows blood to flow back into the left atrium, during systole, while it is being ejected out of the left ventricle. This can create a regurgitation or other mitral valve insufficiency. FIG. 4 further illustrates the valve annulus 205.

Although stenosis or regurgitation can affect any valve, stenosis is predominantly found to affect either the aortic valve 24 or the pulmonary valve 28, whereas regurgitation predominantly affects either the mitral valve 22 or the tricuspid valve 26. Both valve stenosis and valve regurgitation increase the workload on the heart 10 and can lead to very serious conditions if left un-treated; such as endocarditis, congestive heart failure, permanent heart damage, cardiac arrest, and ultimately, death. Since the left heart is primarily responsible for circulating the flow of blood throughout the body, malfunction of the mitral valve 22 or aortic valve 24 is particularly problematic and often life threatening. Accordingly, because of the substantially higher pressures on the left side of the heart, left-sided valve dysfunction is much more problematic.

All of the references cited in this application are incorporated by reference in their entireties.

SUMMARY OF THE INVENTION

The present application describes methods and devices for minimally invasive, beating-heart, valve repair, including but not limited to mitral valve repair.

Valve dysfunction can be treated through the placement of artificial chordae between the leaflets and the ventricular wall or papillary muscles or the approximation of leaflets.

An expandable element can be inserted through a valve leaflet, such as a mitral valve leaflet, in order to connect the leaflet to other tissue of the heart, including other leaflets. Artificial chords can be secured to the leaflets without relying on additional manipulations on the atrial side of the valve leaflets.

The exemplary embodiments disclosed herein refer to an apparatus having at least two pledgets, a first line, and at least a second line. The first line can have a first end connected to a first of the at least two pledgets and a second end connected to a second of the at least two pledgets. The second line can be connected to the first line. The at least two pledgets and the first and second lines can be positioned inside a hollow elongate tube. The hollow elongate tube can be a needle.

The exemplary embodiments disclosed herein refer to a method having the steps of introducing a needle into a heart ventricle; contacting the ventricular side of a heart valve leaflet with the needle; piercing the heart valve leaflet with the needle so that at least a portion of the needle extends through the heart valve leaflet; deploying a pledget with a line attached to it on the atrial side of the heart valve leaflet; and withdrawing the needle from the heart valve leaflet back into the ventricle. The needle can have an opening such that when the needle pierces the leaflet, the portion of the needle with the opening passes through to the atrial side of the heart valve leaflet. The pledget and line attached to the pledget can be deployed from the needle through the opening.

The exemplary embodiments disclosed herein further refer to a method having the steps of introducing a catheter with a suction cup at its distal end into a heart ventricle proximate to a heart valve leaflet; contacting a ventricular side of the heart valve leaflet with a distal end of the suction cup; applying a negative pressure to the ventricular side of the heart valve leaflet; extending a needle out of the distal end of the catheter and suction cup; piercing the heart valve leaflet with the needle, deploying a pledget through the opening of the needle on the atrial side of the heart valve leaflet; withdrawing the needle from the heart valve leaflet into the catheter; and releasing the negative pressure to remove the suction cup from the ventricular side of the heart valve leaflet. The needle can be positioned within the catheter. The needle has an opening, and when the leaflet is pierced with the needle, the opening in the needle passes through the leaflet to the other side of the leaflet. A line is secured to the pledget. When the needle is withdrawn from the leaflet, the pledget and at least a portion of the line that is secured to the pledget remain on the other side of the leaflet.

The exemplary embodiments disclosed herein further refer to a method of coapting valve leaflets having the steps of introducing into a needle into a heart ventricle; contacting a ventricular side of a first heart valve leaflet with the needle; piercing the first heart valve leaflet with the needle; withdrawing the needle from the first heart valve leaflet contacting a ventricular side of a second heart valve leaflet with the needle; piercing the second heart valve leaflet with the needle; deploying a second pledget through the opening of the needle on the atrial side of the second heart valve leaflet; withdrawing the needle from the second heart valve leaflet; and withdrawing the needle from the ventricle. Piercing the leaflets includes pushing at least a portion of the needle all the way through to the space on the other side of the leaflet. The needle can have an opening, and the portion of the needle with the opening can be pushed through to the other side of the leaflet. The other side of the leaflet can be the atrial side of the leaflet, when the needle makes initial contact with the ventricular side of the leaflet prior to piercing. Deploying a pledget includes deploying a pledget from the opening in the needle. A line can be attached to the pledget such that both the pledget and a portion of the line remain on the other (for example, atrial) side of the leaflet. After the needle is withdrawn from one leaflet, it can pierce a second leaflet, and the method can repeat so that a second pledget and a portion of the line remains on the other (for example, atrial) side of the second leaflet.

These and aspects of the exemplary embodiments will become apparent from the following detailed description, taken in conjunction with the accompanying drawings, illustrating by way of example the principles of the various exemplary embodiments.

BRIEF DESCRIPTION OF THE DRAWINGS

In order to facilitate a fuller understanding of the exemplary embodiments, reference is now made to the appended drawings. These drawings should not be construed as limiting, but are intended to be exemplary only.

FIGS. 9A-9F depict a needle approaching and puncturing cardiac tissue, deploying a pledget, and removal of a needle in accordance with an exemplary embodiment.

DETAILED DESCRIPTION OF EMBODIMENTS

The following description is intended to convey a thorough understanding of the embodiments by providing various embodiments and details involving a device and method for delivering a suture line and pledgets to repair a mitral valve by replacing one or more chordae with suture line. In various embodiments, the device can also be used in a method for approximating the valve leaflets together. It is understood, however, that the invention is not limited to these specific embodiments and details, which are exemplary only. It is further understood that one possessing ordinary skill in the art, in light of known devices, systems and methods, will appreciate the use of the invention for its intended purposes and benefits in any number of alternative embodiments.

There is a significant need to perform mitral valve repairs using less invasive procedures while the heart is still beating. Accordingly, there is a continuing need for new procedures and devices for performing cardiac valve repairs, such as mitral and tricuspid valve repairs, which are less invasive, do not require cardiac arrest, and are less labor-intensive and technically challenging. Chordal replacement procedures and artificial chordae that ensure the appropriate chordal length and spacing so as to produce a competent valve are of particular interest. The methods and repair devices presented herein meet these needs.

Repair of the chordae of a cardiac valve, such as that provided by the methods described herein, assist the valve leaflets such that they can meet in the correct position, and the valve can once again function properly. This will repair the leaking of the valve, and then in turn alleviate the symptoms associated with such leaking, regurgitation, or other insufficiency.

Figure 1:
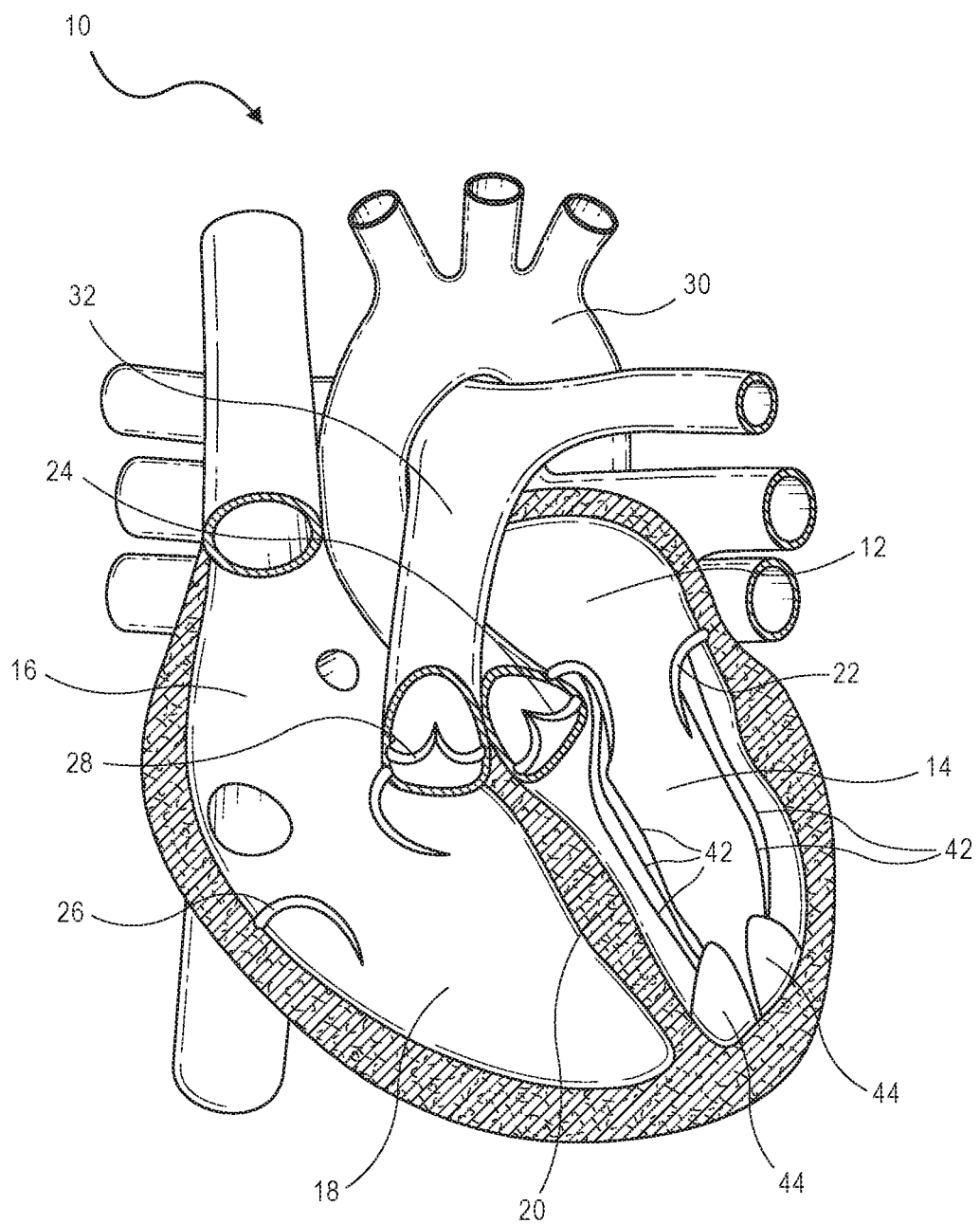
FIG. 1 depicts a cut-away anterior view of the human heart in diastole.
Figure 2:
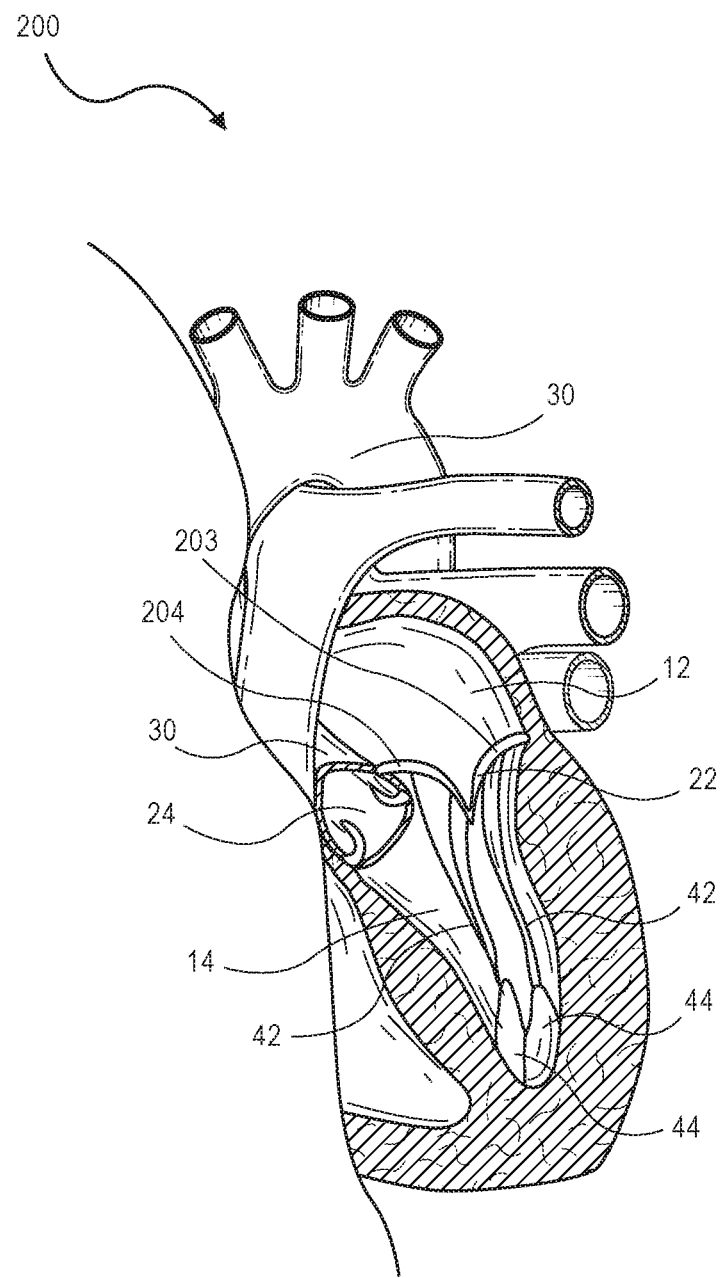
FIG. 2 depicts a cut-away anterior view of the left portion of a human heart in systole.
Figure 3:
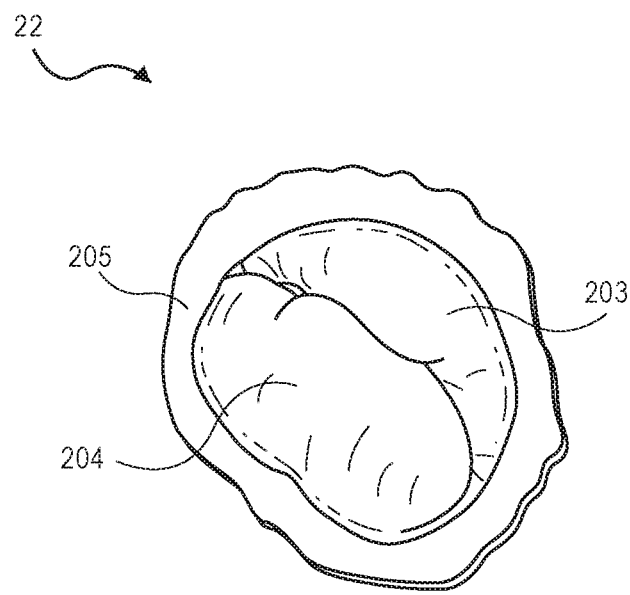
FIG. 3 depicts a top view of a healthy mitral valve with the leaflets closed.
Figure 4:
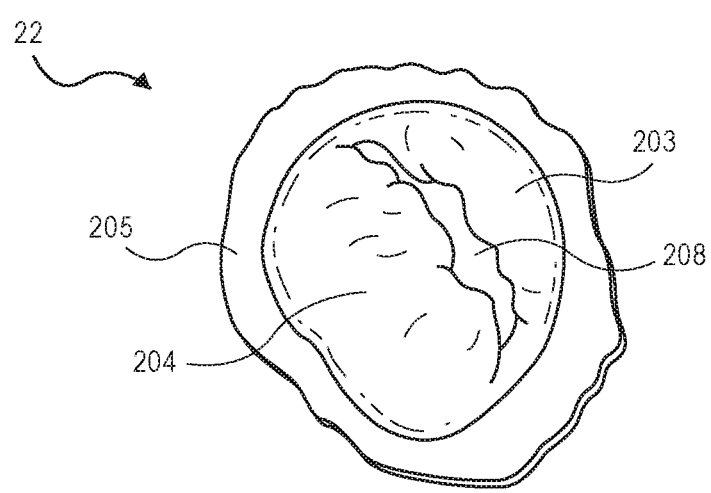
FIG. 4 depicts a top view of a dysfunctional mitral valve with a visible gap between the leaflets.
Figure 5:
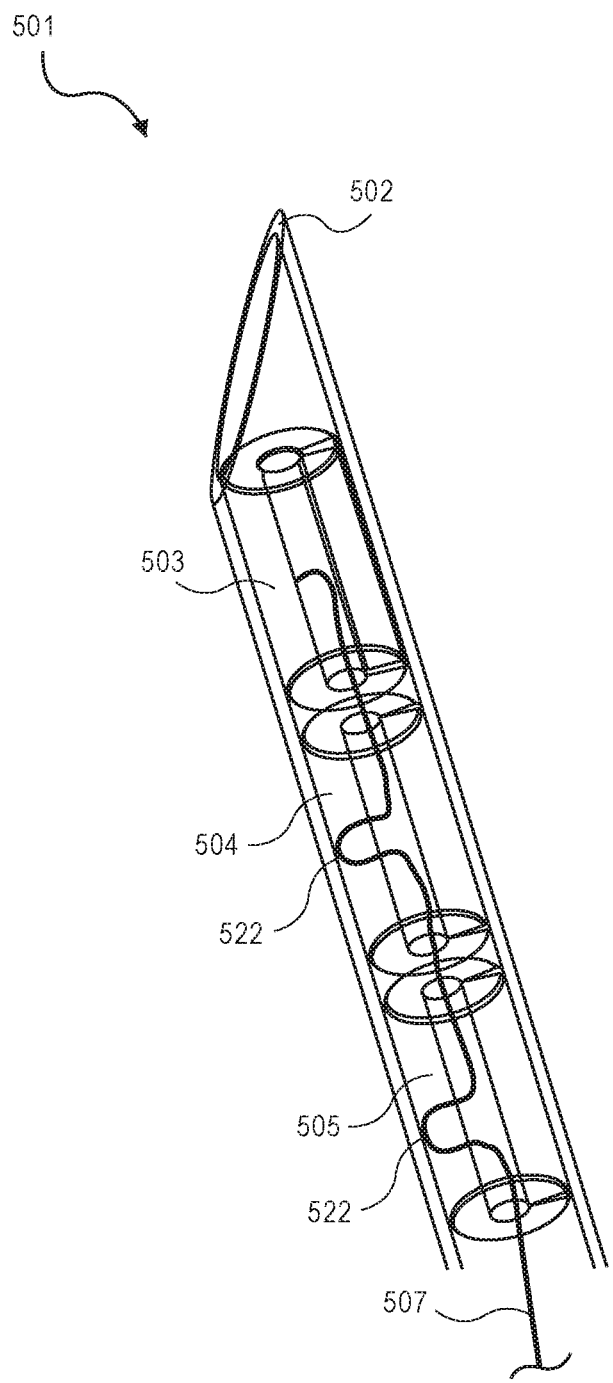
FIG. 5 depicts a perspective view of a needle with pledgets in accordance with an exemplary embodiment.
Figures 10A, 10B:
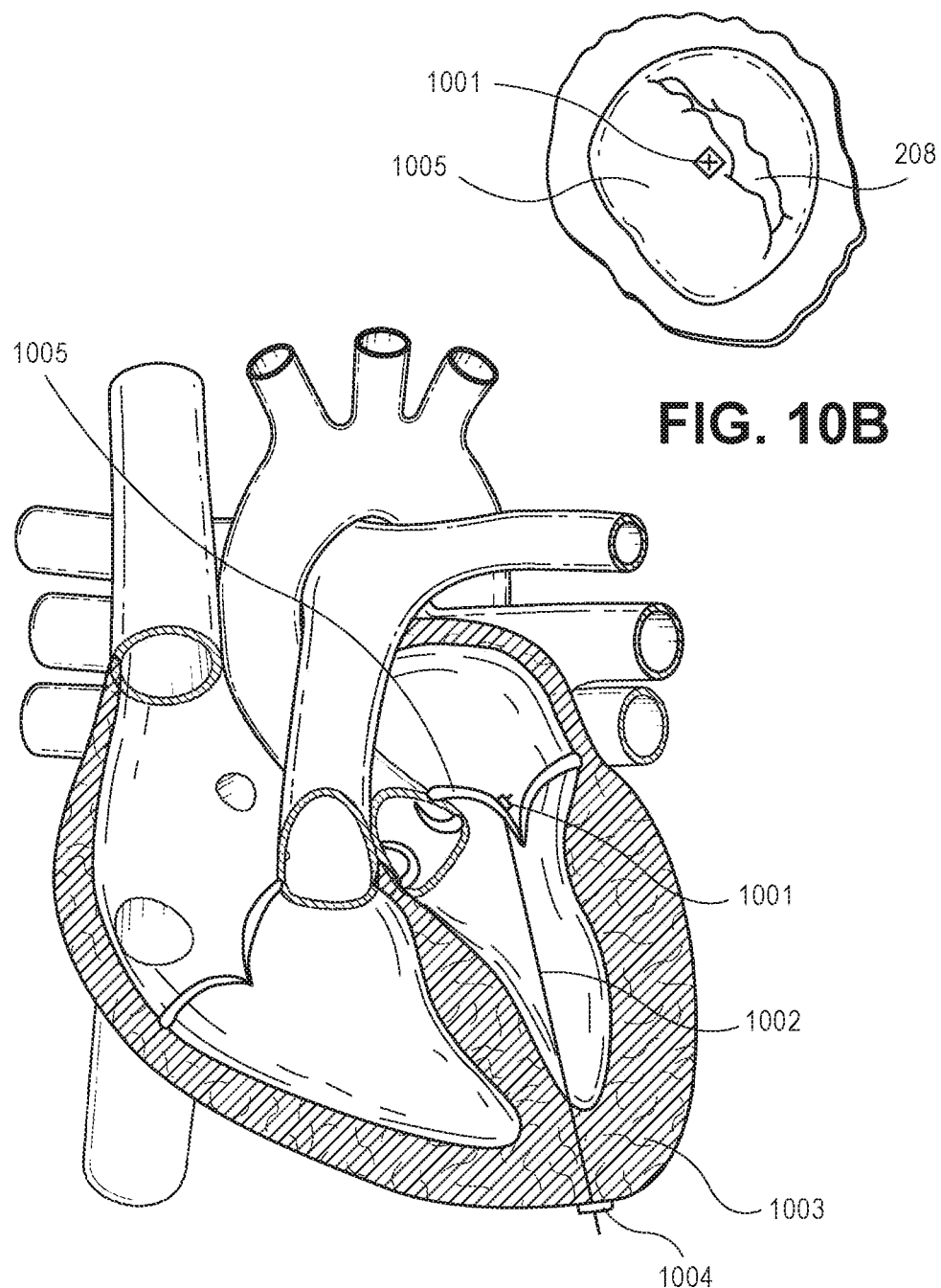
FIG. 10A depicts a cutaway anterior view of a human heart with a pledget and line implanted in accordance with an exemplary embodiment.
FIG. 10B depicts a top view of the pledget of FIG. 10A, on top of a mitral valve leaflet.

Referring to FIGS. 5, 10A, and 10B, the exemplary embodiments disclosed herein use a needle 501 such as a hypotube needle, loaded with a line 507 of chordae replacement material, such as a strand of suture line. The line 507 can be any of a suture, suture line, strand, and/or artificial chordae. The line can be made from a wide variety of different materials. For example, the line 507 can be made of ePTFE or other chordae replacement material with one or more pledgets threaded onto the line. For a ventricular approach, the needle is passed into the heart and through the valve leaflet at the desired location.

Referring to FIG. 5, an exemplary embodiment of a hypotube needle 501 is illustrated. The hypotube needle 501 of FIG. 5 has a sharpened tip 502 and is generally hollow and cylindrical in an exemplary embodiment, with an angled distal end. Inside the needle are a plurality of pledgets 503, 504, 505 which are rolled, folded, or in any other storage or compressed configuration to allow for storage inside the needle and easy deployment. There can be any number of pledgets. The pledgets 501 are connected to one or more lines 507. The configuration of the pledgets and/or the line(s) can be adjusted based on the application. For example, the pledget can be rectangular (see FIG. 6) and can be compressed or rolled (see FIG. 5) to fit within the needle. Groups of two or more pledgets can be provided on a strand 507, allowing for the groups of pledgets to be pulled taught at specific locations. The pledgets 503, 504, 505 can be attached to each other by a line 507, or at least one pledget can be attached to at least one separate line. The line 507 can be secured to the distal most pledget at 503 and slidably run through a center or other location 522 of each of the more proximally located pledgets in the needle as illustrated. The line can be secured (e.g., not slideable) to both the distal-most pledget and the proximal-most pledget. A separate strand 507 can be connected to each pledget 503, 504, 505, or one strand can be connected to two or more pledgets. The pledgets can be crimped and compressed to occupy less volume in a central shaft of the needle, allowing for a reduced outer diameter of the needle 501.

Figure 6:
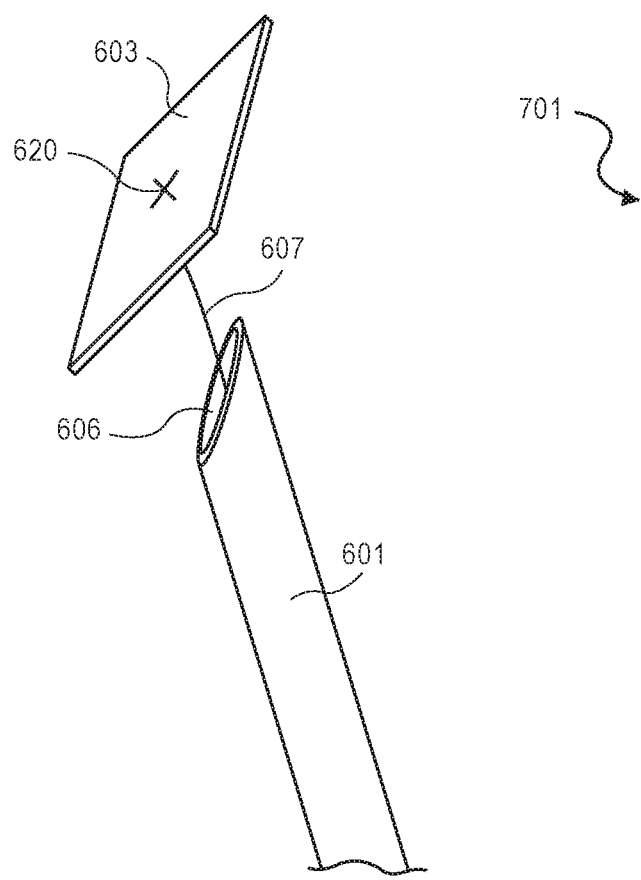
FIG. 6 depicts a perspective view of a needle with a pledget and a line in accordance with an exemplary embodiment.

Referring to FIG. 6, a perspective view of a hypotube needle 601, a line 607, and a deployed and expanded pledget 602 in accordance with an exemplary embodiment is illustrated. The pledget 602 can be square or rectangular in shape, or can be circular or any other shape. For example, the pledget can have a generally flat top surface area and bottom surface area, so as to allow the pledget to act as an anchor on one side of heart tissue 905 (see FIG. 9F). The pledget 602 can be any material suitable for implantation and that is biocompatible, such as PTFE, ePTFE, felts made of PTFE and/or ePTFE, polyester, polyethylene terephthalate (PET, DACRON®), or other polymer. The strand can extend through the pledget, and can be secured by a knot or other means as indicated at 620. In the exemplary embodiment of FIG. 6, the pledget 603 and line can be deployed by pushing the pledget out a distal opening 606 in the needle 601 in exemplary embodiments. The line can be made of any suitable material, for example, PET, ePTFE, or PTFE.

Figure 7:
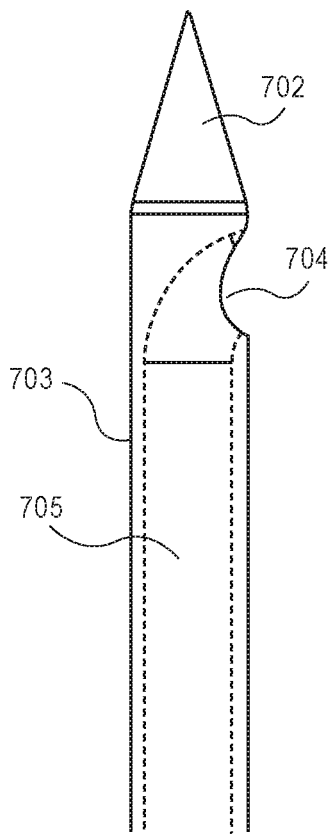
FIG. 7 depicts a side view of a needle in accordance with an exemplary embodiment.

Referring to FIGS. 6 and 7, the pledget 603 and line 607 can also be deployed by pushing the pledget out a side opening 704 of a needle 701. In the example illustrated by FIG. 7, hypotube needle 701 can have a tapered or conical tip 702 at the distal end, for penetrating and dilating tissue. Hypotube needle 701 also has a hollow central lumen 705 and a generally cylindrical body 703. Pledgets can be stored in the central lumen 705 in the manner illustrated in FIG. 5 or in any other manner. The opening 704 is in the side of the cylindrical body just proximal to the conical tip 702. The opening 704 is in fluid connection with the central shaft, in which the pledget(s) and line(s) can be dispensed through. The needle can be made of stainless steel or any other suitable material for needles for surgical use.

Figure 8A:
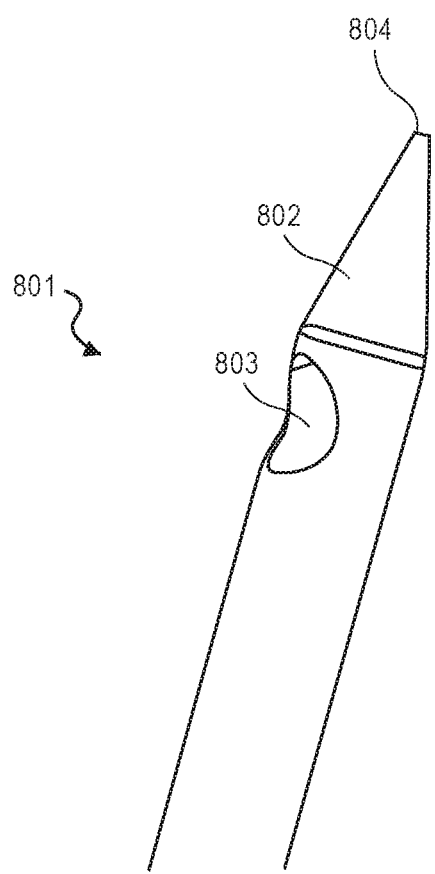
FIGS. 8A and 8B depict views of a needle with a puncturing tip retracted and exposed, respectively, in accordance with an exemplary embodiment.
Figure 8B:
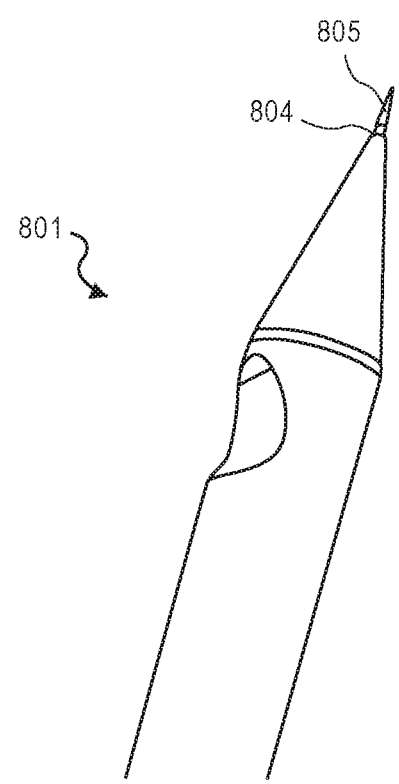

FIGS. 8A and 8B are perspective views of an embodiment of a needle 801. In the example illustrated by FIGS. 8A and 8B the hypotube needle 801 has a conical distal portion 802, and side opening 803 for the deployment of lines and pledgets, and an opening at the distal end 804 of the conical distal portion 802. FIG. 8B illustrates the same needle as FIG. 8A, where the opening 804 at the distal end 804 of the conical tip has a piercing element 805 extending therefrom. The piercing element 805 can be an auto incisor in an exemplary embodiment. The auto incisor can be a spring-loaded retracting point or blade, which allows the placement of the blunt tip of distal portion 802 against the cardiac tissue to be punctured, the location to be verified, and the puncture of the tissue to occur only when the piercing element 805 is extended by an actuator. FIG. 8A illustrates the needle with the auto incisor retracted, and FIG. 8B illustrates the auto incisor in a deployed position. The needle in FIGS. 8A and 8B can be used in any of the procedures described herein, including but not limited to inserting artificial chordae and securing opposing edges of two or more leaflets together.

FIGS. 9A-9F illustrate the steps involved in the deployment of a line 909 and single pledget 906 in a cardiac tissue 905. For example, a valve leaflet, such as a mitral valve leaflet or a tricuspid valve leaflet. The line 909 can be used as an artificial mitral valve or tricuspid valve cord or to secure two or more leaflets together (e.g., Alfieri procedure). In this embodiment, a shafted instrument 901, which can be a hyponeedle, is inserted into the cardiac tissue 905 to deploy a pledget 906. In the example, the needle 901 has a conical distal end 902 with an opening 904 towards the distal-most end 912, which is flat or otherwise non-tissue-piercing, and a side opening 910 along a hollow shaft 911. However, any of the needles disclosed herein can be used to perform the method illustrated by FIGS. 9A-9F. In FIG. 9A, the flat distal tip 912 is brought close to the cardiac tissue 905, which can be mitral valve leaflet tissue. FIG. 9B illustrates the same needle 901 after it has been moved closer to the tissue, and flat distal tip 912 now makes contact with tissue 905. FIG. 9C illustrates a needle 901 with a piercing element 913 extended from the distal end of the conical portion, puncturing the tissue 905 as illustrated herein. FIG. 9D illustrates the needle 901 with the conical tip 902 and the side opening 910 fully inserted through the cardiac leaflet tissue 905. FIG. 9E illustrates a pledget 906 attached to a line 909 deployed such that the pledget is in an expanded configuration. FIG. 9F illustrates the withdrawal of the needle 901 from the cardiac leaflet tissue 905 and pulling the line 909. For example, the line can pull the pledget 906 against leaflet tissue 905.

Referring to FIG. 10A, in an exemplary embodiment, the pledget 1001 abuts the atrial side of a mitral valve leaflet 1005. The pledget can be brought into contact with the atrial side of the leaflet 1005, for example, once the delivery device or needle 901 has been removed from the heart ventricle or after the needle has been removed from the leaflet 1005. The line 1002 is then pulled taught, and the line is anchored to the outside of the ventricular wall at or near the point of entry into the ventricle, for example, the apex, with an anchor 1004.

FIGS. 10A-10B illustrate an exemplary embodiment of a single pledget inserted into the mitral valve leaflet tissue. In FIG. 10A, a single pledget 1001 attached to a single line 1002 has been implanted. The line 1002 is visible in the left ventricle of this cutaway anterior view of the human heart. The line is anchored into the ventricular wall 1003 of the left ventricle. The anchor 1004 can also be placed into or through the papillary muscle at the discretion of the user. The anchor can be another pledget in an exemplary embodiment. The anchor can be any one or plurality of a pledget, knot, clip, disc, hook, barb, and/or adhesive. Any device capable of securing the line 1002 to the heart tissue can be used. The line can replace or work in conjunction with existing chordae.

FIG. 10B illustrates the top view of the mitral valve, with the pledget 1001 abutting the atrial surface of the anterior leaflet 1005 of the mitral valve. In FIGS. 10A-10B, a single pledget is deployed from a needle, and the line is anchored via anchoring element 1004 near the outside of the apex of the heart such that the line is of an appropriate length to be a replacement or supplemental chordae in the ventricle of the heart. In an exemplary embodiment, the leaflet 1005 is imaged and the length of the line 1002 is adjusted to reduce or eliminate prolapse of the leaflet 1005 and/or the gap 208 illustrated by FIG. 10B. For example, a leaflet may be imaged by echocardiography (echo), which can also be used to detect regurgitation.

Figure 11:
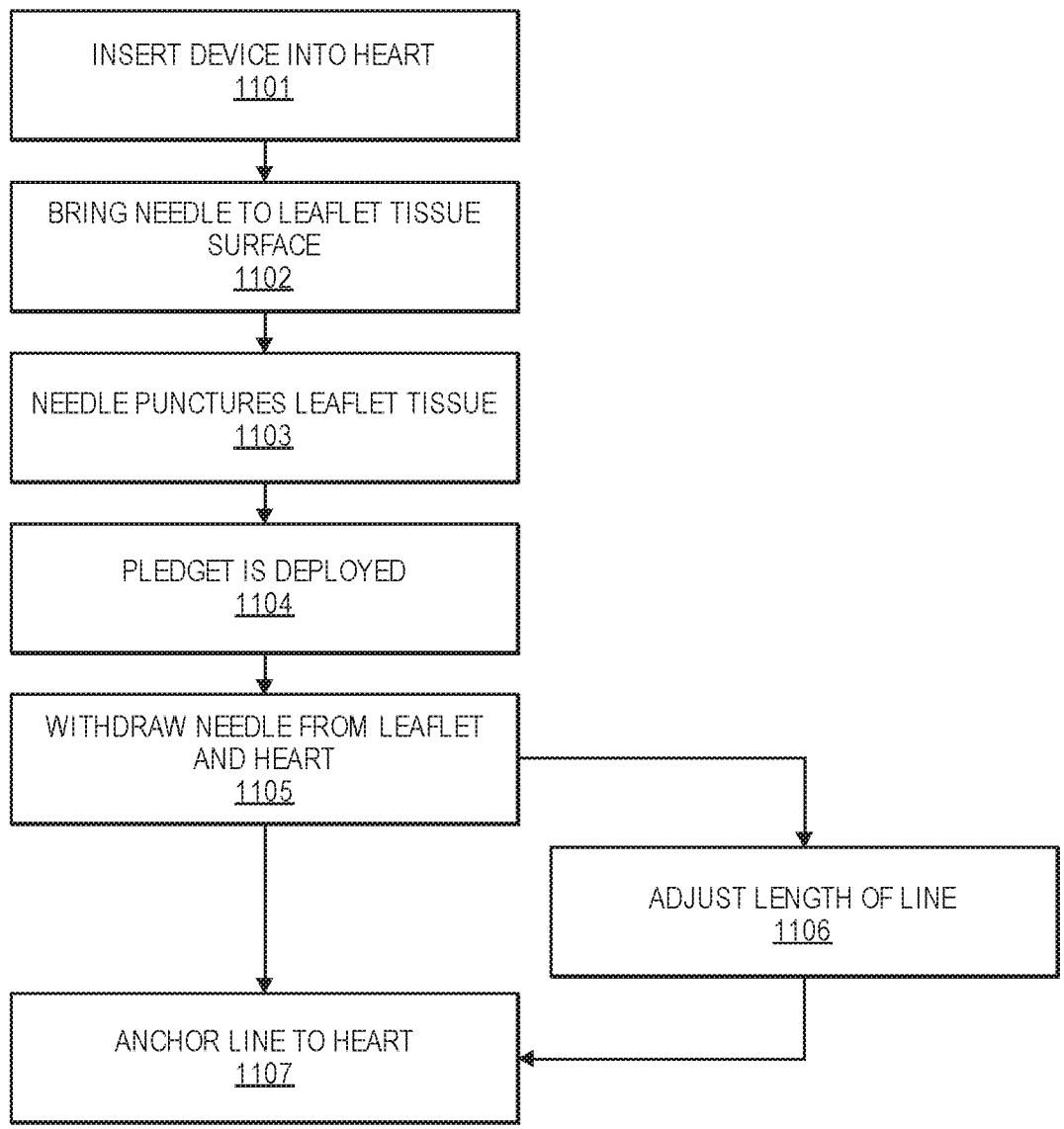
FIG. 11 depicts an exemplary embodiment of a method of implantation in accordance with the exemplary embodiment of FIGS. 10A and 10B.

An exemplary method for inserting the pledgets and line by deploying the line and at least one pledget from a hypotube needle as illustrated in FIGS. 10A-10B is shown in FIG. 11. In step 1101, the needle, which can be contained within a delivery device, can be inserted through the ventricle of the heart, near the apex of the heart or any other location as deemed appropriate by the user. The needle is passed into the heart and through the valve leaflet to the desired location. Assistance in positioning the needle can be provided by exemplary embodiments of a deployment device with an outer catheter and a suction cup as disclosed herebelow and illustrated in FIGS. 19-23. In step 1102, the needle is brought to the ventricular surface of a valve leaflet. In step 1103, the needle punctures the leaflet tissue until an opening in the needle is on the atrial side of the leaflet. The puncturing of the leaflet can be accomplished using an optional piercing element at the distal end of the needle. In step 1104, a most distal pledget and at least a portion of the line in the needle is deployed on the atrial side of the leaflet. In step 1105, the needle is retracted from the leaflet, and then from the ventricular wall. Here the line is set to its desired length, and the line, now acting as an artificial chord, can be anchored in step 1107 to the ventricular access location with an anchor. In one exemplary embodiment, in optional step 1106, the valve is viewed to confirm that the leaflets are coapting while the heart is beating and the length of the line is adjusted if necessary.

Figure 12B:
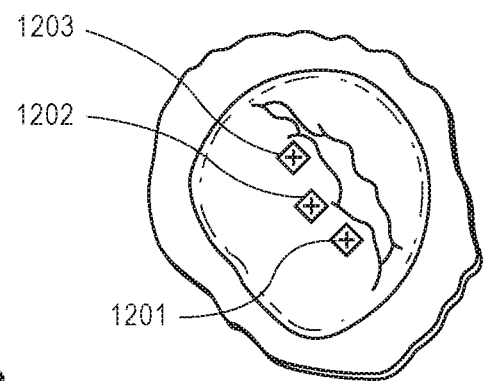
FIG. 12B depicts a top view of the pledgets of FIG. 12A and leaflets of a mitral valve leaflet.
Figure 12A:
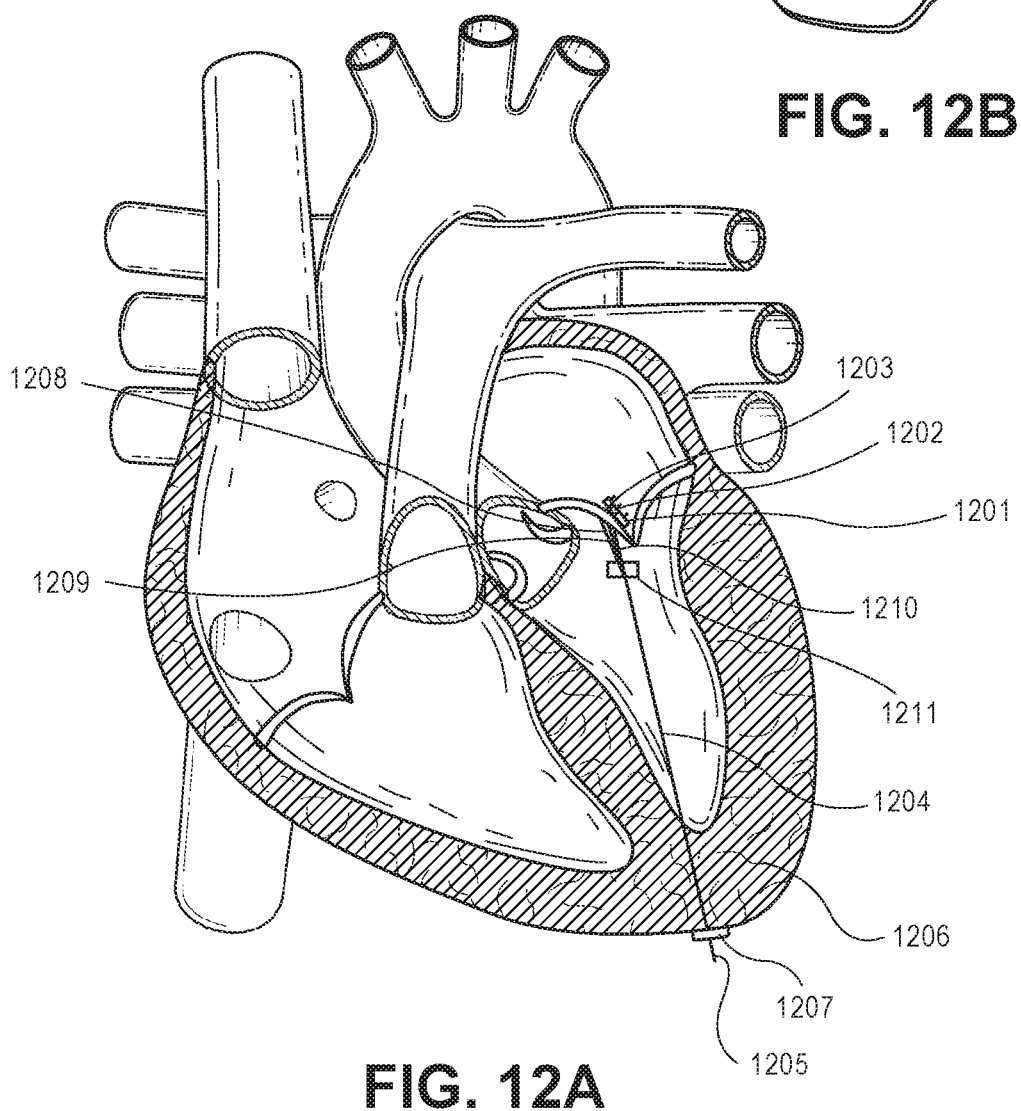
FIG. 12A depicts a cutaway anterior view of a human heart with a plurality of pledgets in accordance with an exemplary embodiment.
Figure 12C:
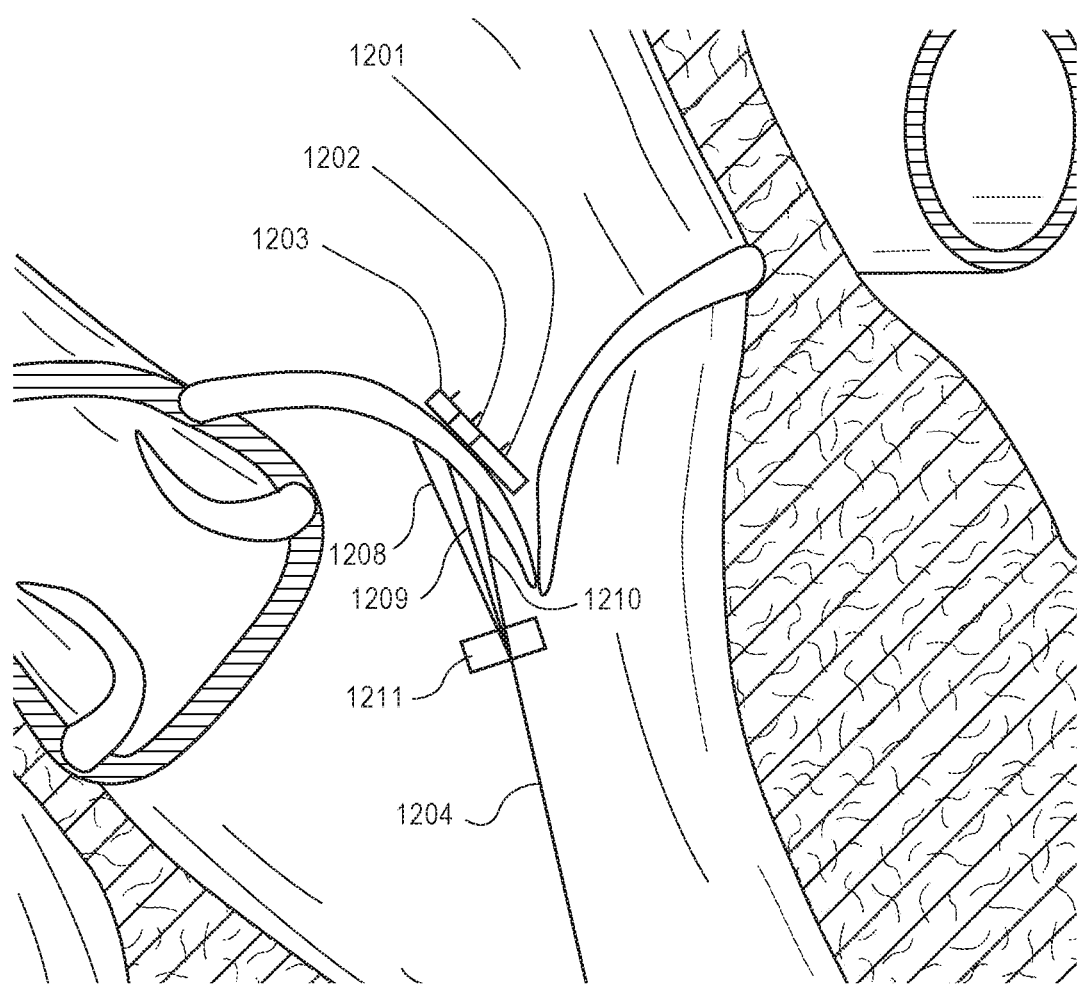
FIG. 12C depicts a close-up of a portion of the view of FIG. 12A.

FIGS. 12A-12C illustrate another exemplary embodiment of pledgets 1201, 1202, 1203 and lines inserted to replace or work in conjunction with a chordae attached to the left ventricle and mitral valve leaflets. FIG. 12A depicts a cutaway anterior view of the human heart, with a single longer line, and a plurality of shorter lines that are each connected to a pledget. FIG. 12C illustrates a close-up of a portion of FIG. 12A. In this configuration, each pledget 1201, 1202, 1203, is fixedly attached to a shorter line. The shorter lines 1208, 1209, and 1210, attached to each pledget, 1201, 1202, and 1203, respectively, are all connected to a longer line 1204. The first pledget 1201 is dispensed through, for example, an opening 704 in a needle 701 of FIG. 7. The needle is then removed from the leaflet tissue and reinserted into the leaflet tissue. Once the opening of the needle is again on the atrial side of the leaflet, a second pledget 1202 is dispensed. The needle is again withdrawn from the leaflet. The needle can be inserted into the leaflet a third time and a third pledget 1203 is dispensed into the mitral valve leaflet. Any number of pledgets can be deployed in this manner. Once the pledgets have been deployed, the needle is again removed from the leaflet. The three lengths of suture line 1208, 1209, and 1210, can be secured to each other and to the longer line 1204, by a connector 1211. The connector can also be stored in the needle for deployment into the heart. The device used to deploy the pledgets and line is withdrawn from the ventricular wall of the heart, and the line 1204 is pulled so that the pledgets are all pulled into contact with the atrial side of the leaflet. The proximal end 1205 of the line 1204 can be secured against the outside of the heart wall 1206 with an anchor 1207 that can be used to adjust the line to its optimal length to have a desired therapeutic effect on the heart valve leaflets and serve as a replacement or complimentary to the chordae to the mitral valve. FIG. 12B illustrates a top view (e.g., from the atrial side) of the mitral valve leaflets, with the first, second, and third pledgets 1201, 1202, 1203 in position in the anterior leaflet 1208.

Figure 13:
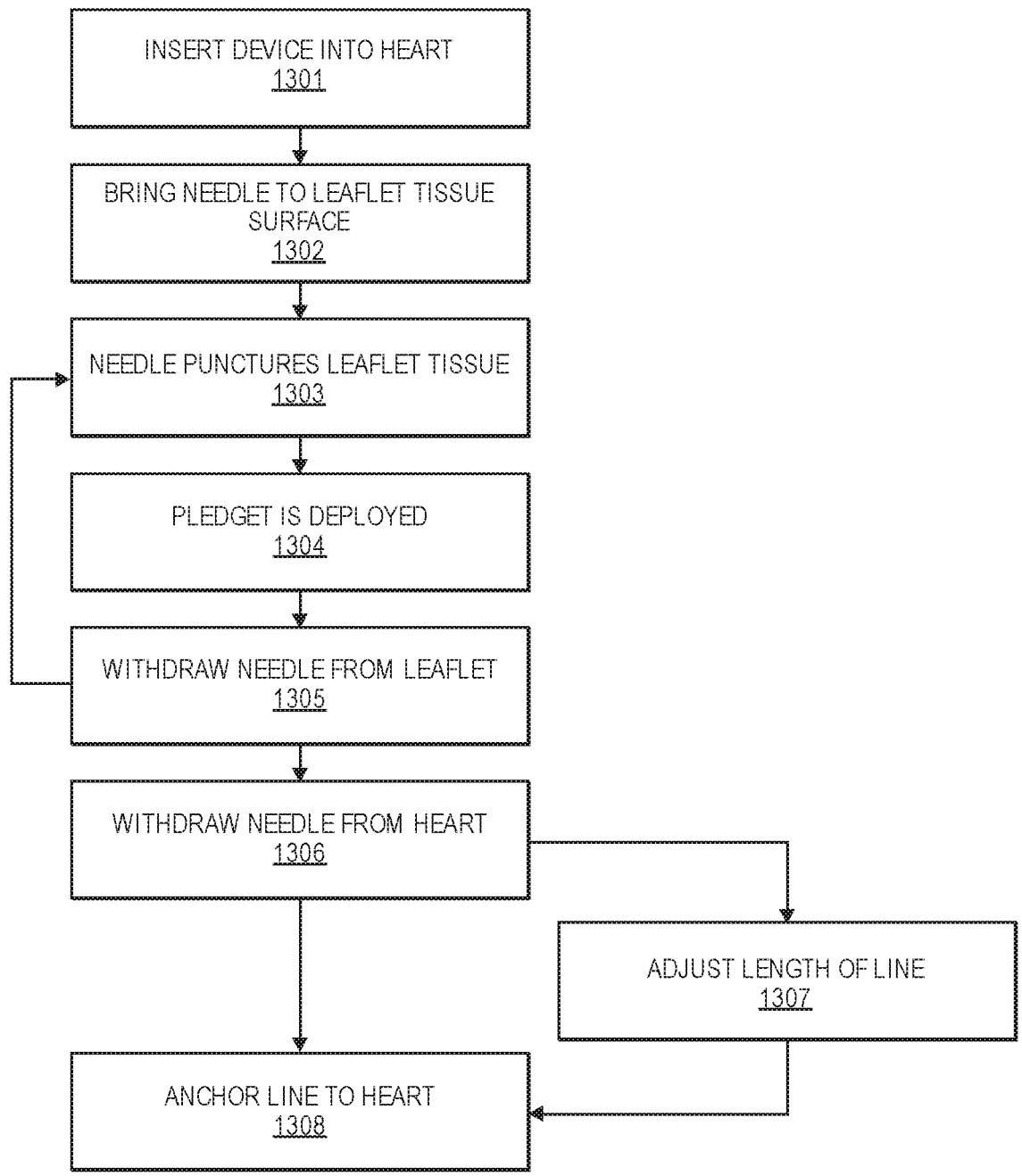
FIG. 13 depicts an exemplary embodiment of a method of implantation in accordance with the exemplary embodiment of FIGS. 12A and 12B.

An exemplary method for deploying pledgets in the configuration disclosed in FIGS. 12A-12C, is shown in FIG. 13. In step 1301 of this exemplary embodiment, the device is inserted through the ventricular wall. In step 1302, the needle is brought to the leaflet tissue on the ventricular side of the leaflet. Assistance in positioning the needle can be provided by exemplary embodiments of a deployment device with an outer catheter and a suction cup as disclosed herebelow and illustrated in FIGS. 19-23. In step 1303, the needle punctures the leaflet and extends through it. In step 1304, a first pledget, securedly attached to the line, is deployed. In step 1305, the needle is removed from the leaflet but is not fully withdrawn from the ventricle. Steps 1303 through 1305 are repeated until a desired number of pledgets and lines have been deployed in the leaflet tissue. A connector piece holds the lines secured to the pledgets together. The connector piece can be dispensed from the needle in the heart ventricle after any withdrawal of the needle from the leaflet. The connector can also be deployed from the needle prior to any contact of or insertion of the needle into the leaflet. The needle and delivery device can be removed from the heart in step 1306. In step 1308, the length of the suture line (or lines) are adjusted so that it is (they are) taught when the valve leaflet is in the closed position. In one exemplary embodiment, the valve is viewed to confirm that the leaflets are coapting while the heart is beating, and the length of the line is adjusted if necessary, shown in step 1307. FIG. 12A illustrates a plurality of pledgets deployed by this method.

Figures 14A, 14B:
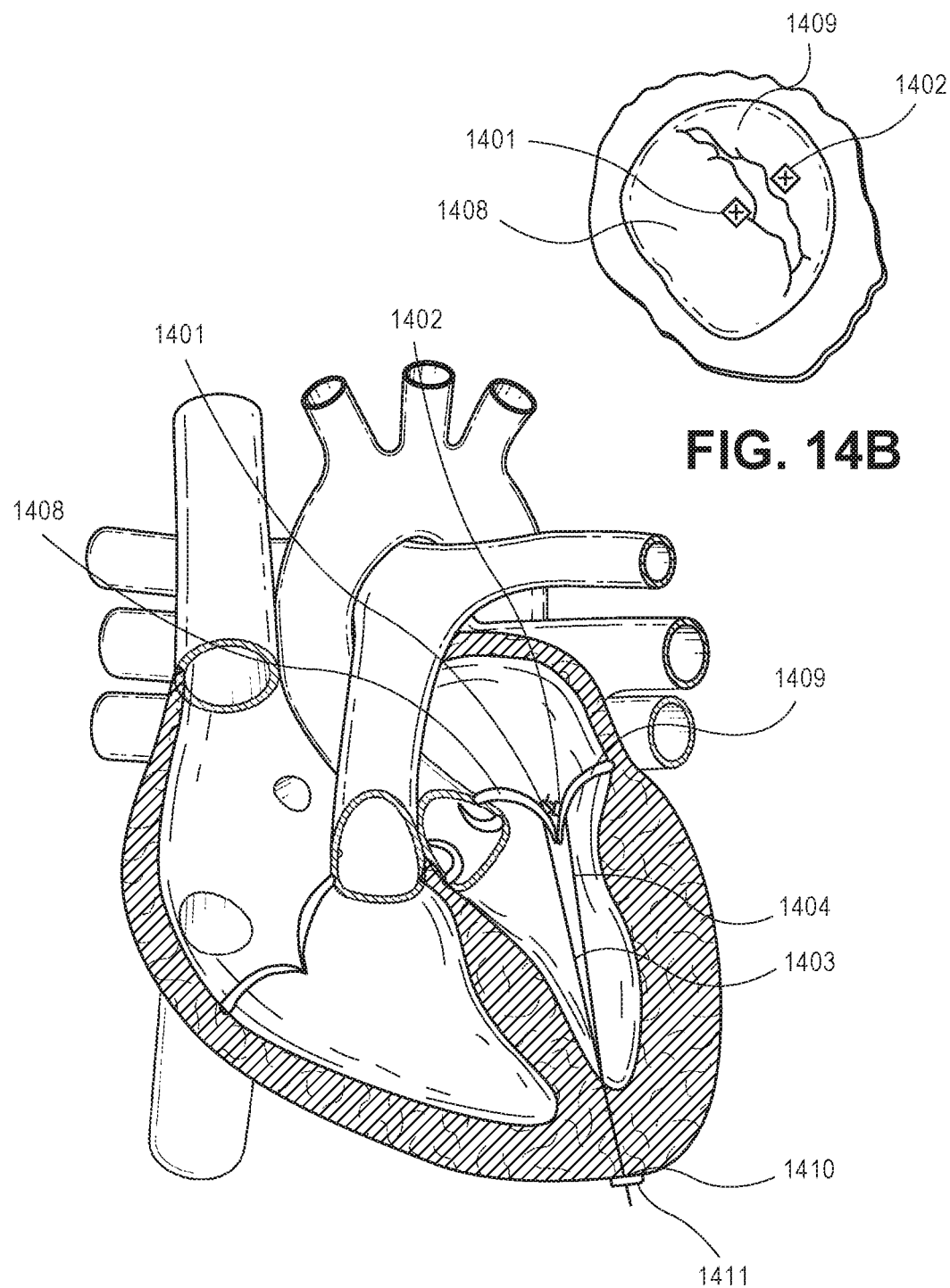
FIG. 14A depicts a cutaway anterior view of a human heart with a plurality of pledgets and sutures in accordance with an exemplary embodiment.
FIG. 14B depicts a top view of the pledgets of FIG. 14A and leaflets of a mitral valve.

FIGS. 14A-14B illustrate another exemplary embodiment of using pledgets 1401 and 1402, and lines 1403, 1404 to repair a mitral valve insufficiency or regurgitation. FIG. 14A illustrates another exemplary embodiment of the implantation of the pledgets. In this embodiment, a single line can be used to deploy pledgets 1401, 1402. The device has been inserted through the ventricular wall, the needle inserted through the anterior mitral valve leaflet, and a pledget 1401 deployed. The device is then removed through the ventricular wall, and the line 1403 secured with an anchor 1411. The device is then reinserted through the ventricular wall at approximately the same or the exact same location as the first time, then the needle is brought up to the posterior leaflet, puncturing it and deploying another pledget 1402. The needle and device are then retracted from the heart, and the line 1404 is secured with anchor 1411. In this way, a plurality of lines 1403, 1404, can be implanted in the heart's ventricle, all from a single piece of suture line, and tethered at the same anchoring location 1410. Any number of pledgets and lines can be deployed. FIG. 14B illustrates a top view of the mitral valve, having a pledget 1401 abutting the atrial side of the anterior leaflet 1408, and a pledget 1402 abutting the atrial side of the posterior leaflet 1409.

Figure 15:
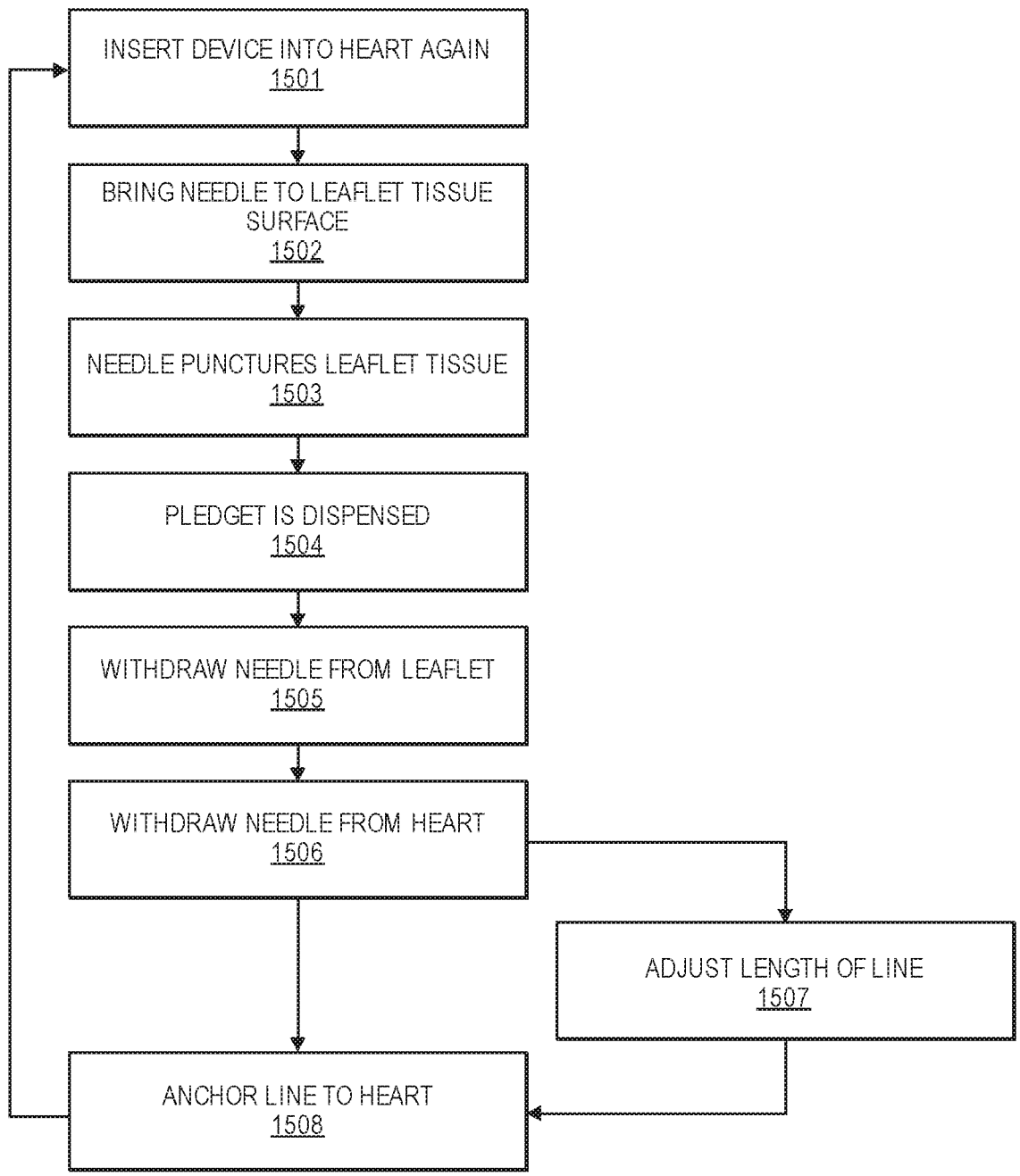
FIG. 15 depicts an exemplary embodiment of a method of implantation in accordance with the exemplary embodiment of FIGS. 14A and 14B.

FIG. 15 illustrates an exemplary embodiment of a method for inserting a plurality of pledgets off of a single line. Multiple lines can be positioned in the heart, from a single anchoring location. Assistance in positioning the needle can be provided by exemplary embodiments of a deployment device with an outer catheter and a suction cup as disclosed herebelow and illustrated in FIGS. 19-23. Once a first pledget and line have been positioned, as in steps 1101 through 1106 of FIG. 11, the device can be pulled back through the ventricle, in step 1501, and the line can be held external to the heart while the device is passed back into the ventricle. In step 1502 the needle is brought into contact with the leaflet tissue in a desired location. In step 1503, the needle punctures the valve leaflet again; and in step 1504 another pledget is deployed on the atrial side of the leaflet. In step 1505, the needle is removed from the leaflet, and in step 1506, the needle and device are withdrawn back through the ventricular wall. In this way, a plurality of pledgets, and a plurality of lines, can be positioned in the heart, all from a single piece of line. In step 1508, the lines are anchored to the outside of the heart wall. This process of steps 1501 through 1508 can be repeated as many times as needed to deploy a plurality of pledgets into a leaflet. In one exemplary embodiment, the valve is viewed to confirm that the leaflets are coapting while the heart is beating and the length of the lines is adjusted if necessary, in step 1507. The valve can be viewed after each instance in which the needle is removed from the heart wall, or at any time during the procedure. FIG. 14A illustrates a plurality of pledgets deployed by this method.

Figures 16A, 16B:
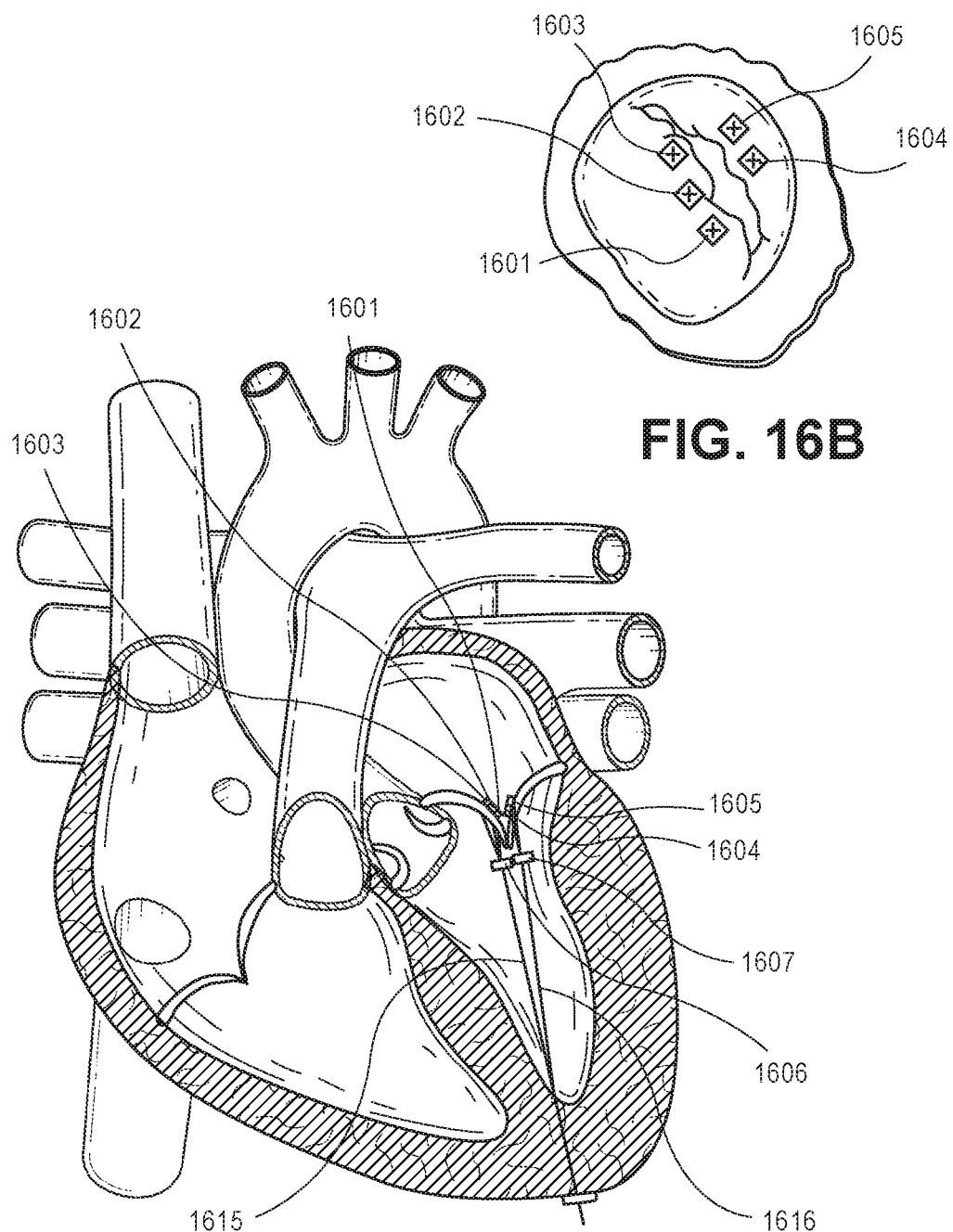
FIG. 16A depicts a cutaway anterior view of a human heart with a plurality of pledgets and sutures in accordance with an exemplary embodiment.
FIG. 16B depicts a top view of the pledgets of FIG. 16A and leaflets of a mitral valve.
Figure 16C:
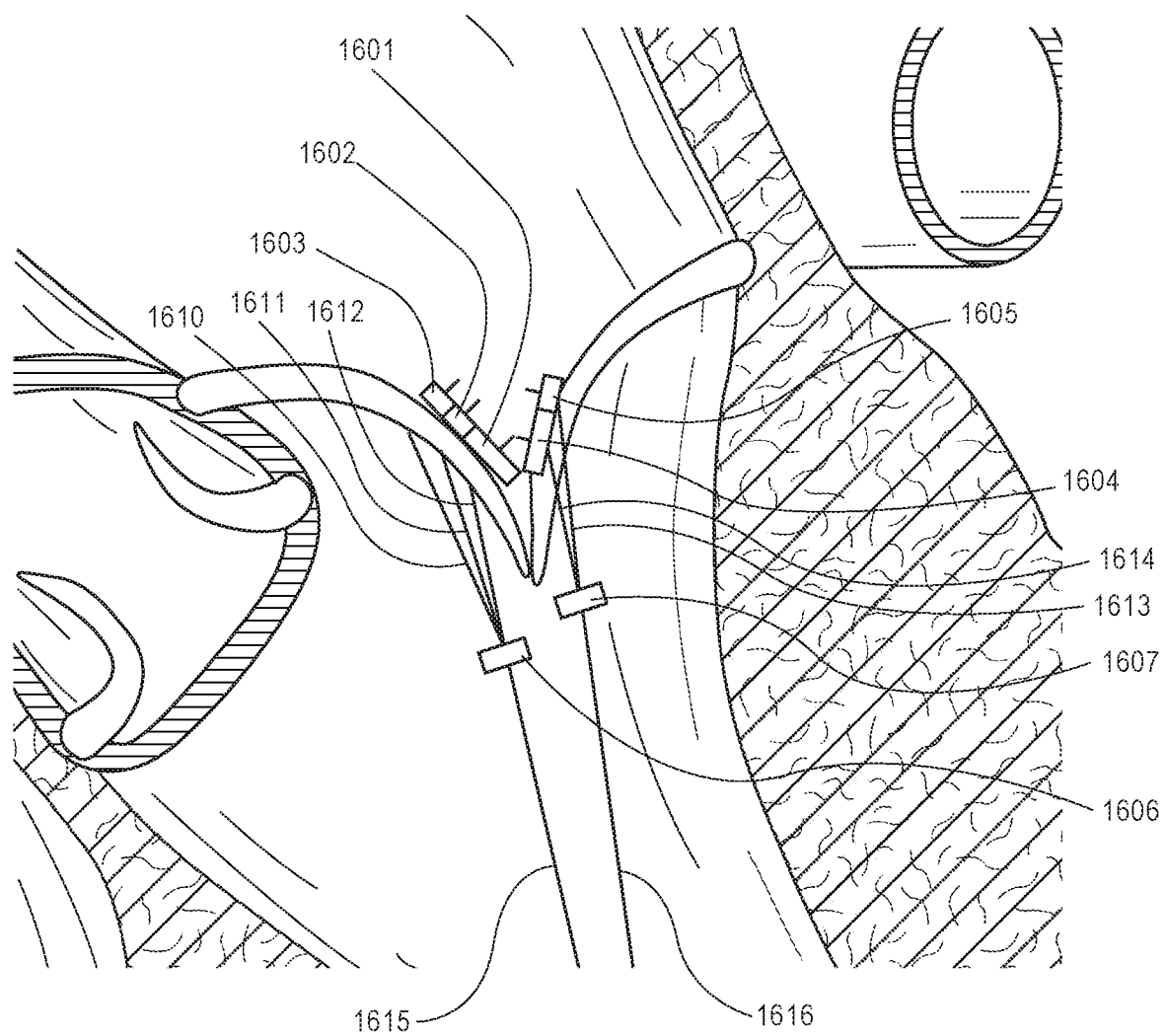
FIG. 16C depicts a close-up of a portion of the view of FIG. 16A.

FIGS. 16A-16C illustrate an insertion of pledgets 1601, 1602, 1603, 1604, and 1605, and lines 1610, 1611, 1612, 1613, 1614, 1615, and 1616, involving a combination of the methods described above. Here, a first insertion of the device is made in the ventricular wall, and a plurality of pledgets are deployed by the needle into the anterior leaflet of the mitral valve while the needle remains in the ventricle, consistent with a method disclosed in FIGS. 12A, 12B, and 13. Assistance in positioning the needle can be provided by exemplary embodiments of a deployment device with an outer catheter and a suction cup as disclosed herebelow and illustrated in FIGS. 19-23. Then the device can be withdrawn from the ventricle, so that the line can be tethered or anchored to the ventricular wall of the heart. The device can then be inserted again through the ventricle, this time with the needle puncturing the posterior leaflet of the mitral valve, and deploying a plurality of pledgets. In FIGS. 16A-16C, three pledgets 1601, 1602, 1603 have been deployed into the anterior leaflet and two pledgets 1604, 1605 have been deployed into the posterior leaflet, but any number and combination of pledgets can be used. FIG. 16C is a close-up view of a portion of FIG. 16A. The pledgets can be deployed in any order. For example, all pledgets deployed in the anterior valve can be deployed followed by deployment of all pledgets into the posterior valve; the posterior valve pledgets can be deployed before the anterior valve pledgets; or the pledgets be deployed in an alternating manner between the leaflets. The lines secured to pledgets can be connected by connectors 1606, 1607. All of the pledgets can be deployed from the same line, or a new line can be used each time the device is deployed into the ventricle. In an exemplary embodiment, lines 1610-1616 are all of the same line of suture material. As with FIGS. 12A-12B and 13, connectors 1606, 1607 can be dispensed from the needle after any withdrawal of the needle from, or prior to the first insertion of the needle to, the anterior leaflet. A connector can be dispensed from the needle after any withdrawal of the needle from, or prior to the first insertion of the needle into, the posterior leaflet.

Figures 17A, 17B:
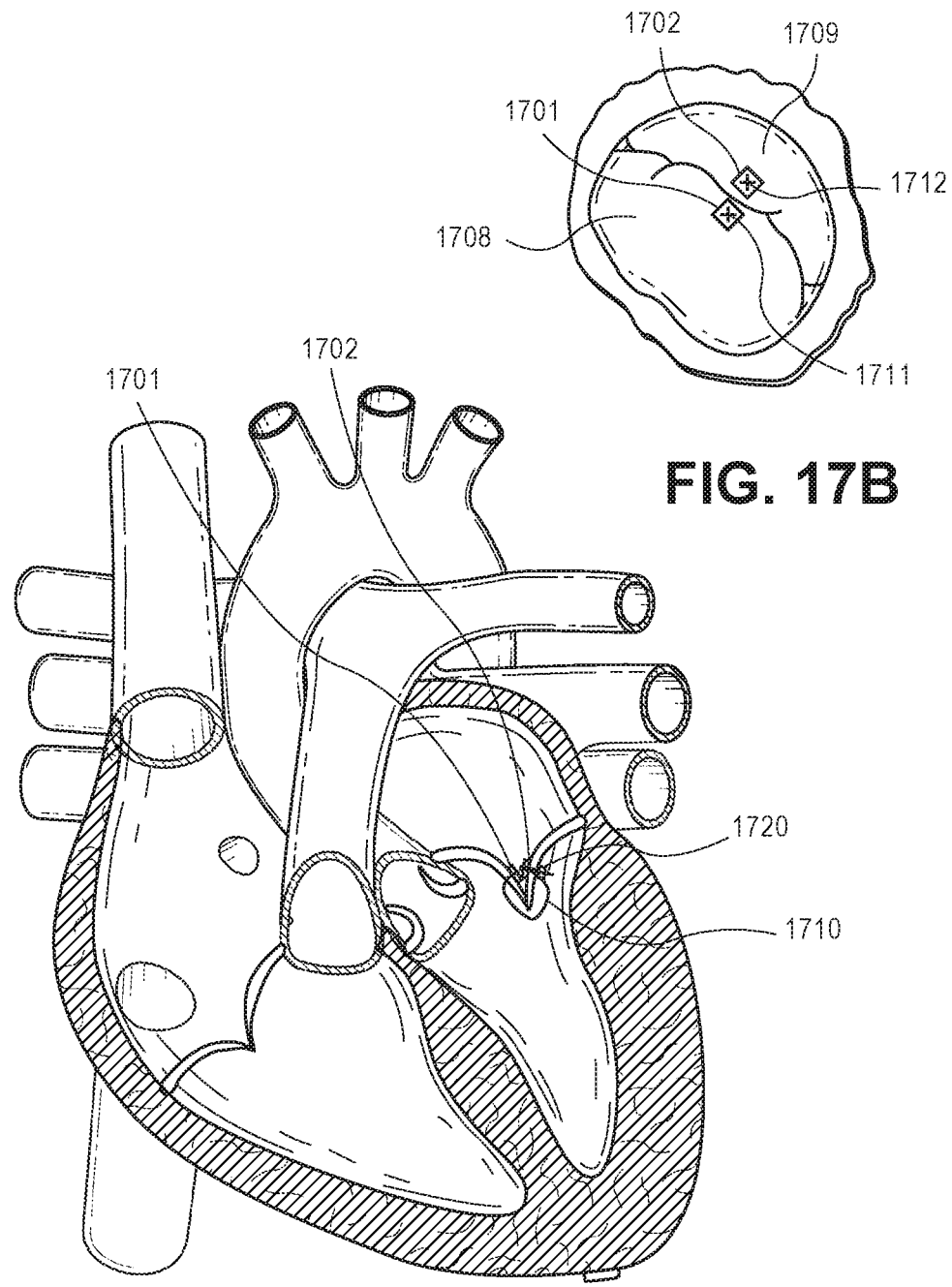
FIG. 17A depicts a cutaway anterior view of a human heart with pledgets coapting mitral valve leaflets together in accordance with an exemplary embodiment.
FIG. 17B depicts a top view of the pledgets of FIG. 17A and leaflets of a mitral valve.
Figure 18:
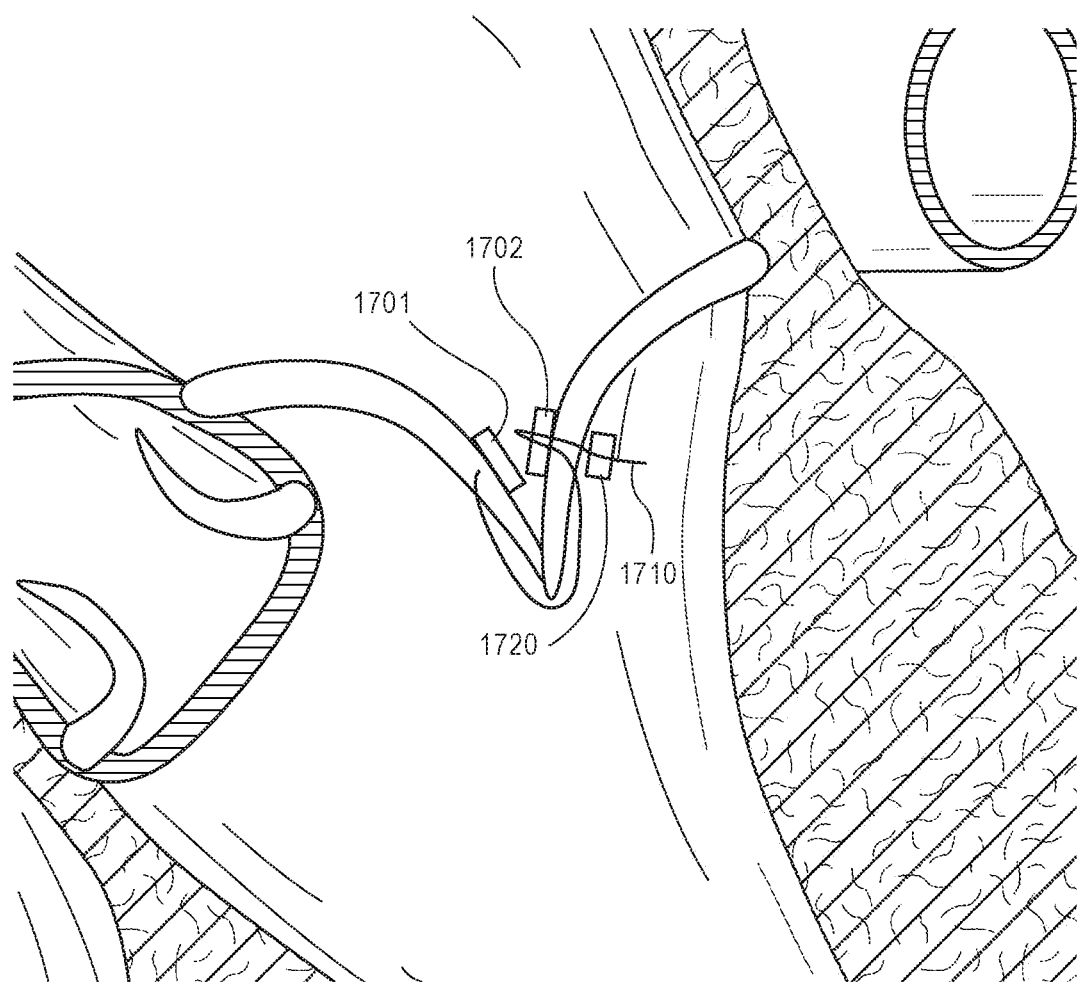
FIG. 18 depicts a close-up of a portion of the view of FIG. 17A.

FIGS. 17A-17B and 18 depict pledgets 1701, 1702 and line 1710 deployed in another manner in accordance with an exemplary embodiment. The illustrated pledgets and line approximate the function of an Alfieri stitch procedure. In FIGS. 17A and 18, a cutaway anterior view of the human heart, two pledgets 1701, 1702 have been inserted, connected by a line 1710. FIG. 18 is a close-up view of a portion of FIG. 17A. Here a single pledget 1701 is positioned such that it abuts the atrial side of the anterior leaflet 1708 of the mitral valve, and a single pledget 1702 is positioned such that it abuts the atrial side of the posterior leaflet 1709 of the mitral valve. The line 1710 extends around the ventricular side of the valve leaflets 1708, 1709. The line 1710 is pulled tight to pull the centers of the leaflets 1708 and 1709 together. A connector 1720 is placed on the ventricular side of the leaflet 1709 to keep the line 1710 tight. The pledgets 1708, 1709 and line or suture 1710 coapt the leaflets together to resolve a mitral valve regurgitation or insufficiency.

The pledgets and line can be initially implanted in the same way as the previous configurations. That is, the device can be inserted through the ventricular wall, and the needle punctures a first leaflet of the mitral valve, followed by a deployment of a first pledget, which is secured to the end of a line. The needle is then withdrawn from the leaflet, and the line can be pulled so that the pledget abuts the atrial side of the leaflet. Then the needle is inserted into the second leaflet of the mitral valve, and a second pledget is deployed. The needle is removed from the second leaflet, and the line is pulled taught such that the second pledget abuts the atrial side of the second leaflet. The line can be secured to the second pledget by the connector 1720 so that once both pledgets are deployed, the line that connects them is on the ventricular side of the mitral valve, and the device can be withdrawn from the heart through the ventricular wall without any further manipulation of line or pledget. The line can also be slidably engaged with the second pledget, and tied, anchored, or otherwise secured against the ventricular side of the mitral valve. Once the needle has been removed from the second leaflet, the line can be sized to the appropriate length. Again, a connector 1720 attached to the suture can be stored in the needle and dispensed in the ventricle of the heart either prior to any insertion of the needle into a leaflet, or after any withdrawal of the needle from a leaflet.

FIG. 17B depicts a top view of a mitral valve where a pledget 1701 on the anterior leaflet 1708 and a pledget 1702 on the posterior leaflet 1709 are abutting the atrial side of the leaflets and are connected on the ventricular side by a suture. The anchoring knots 1711, 1712 of the suture line are visible on top of each of the pledgets. The pledgets can also be secured to the suture in any other suitable way. In FIG. 17B, the valve leaflets are coapted together to hold the centers of the valve leaflets together. The portions of the valve leaflets 1708, 1709, on either side of the pledgets 1701, 1702 will open and close to allow the mitral valve to function. Any number of pairs of pledgets attached by a suture line can be deployed.

Figure 19A:
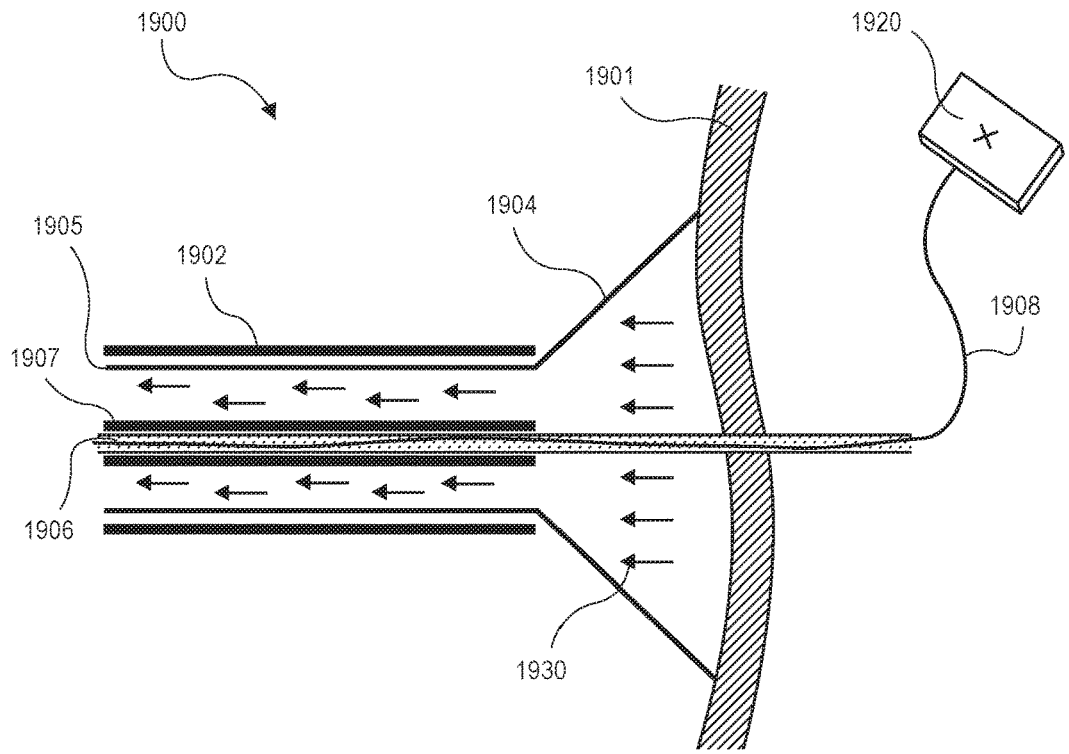
FIGS. 19A and 19B are side cross sections of an embodiment of an artificial chord delivery device.
Figure 19B:
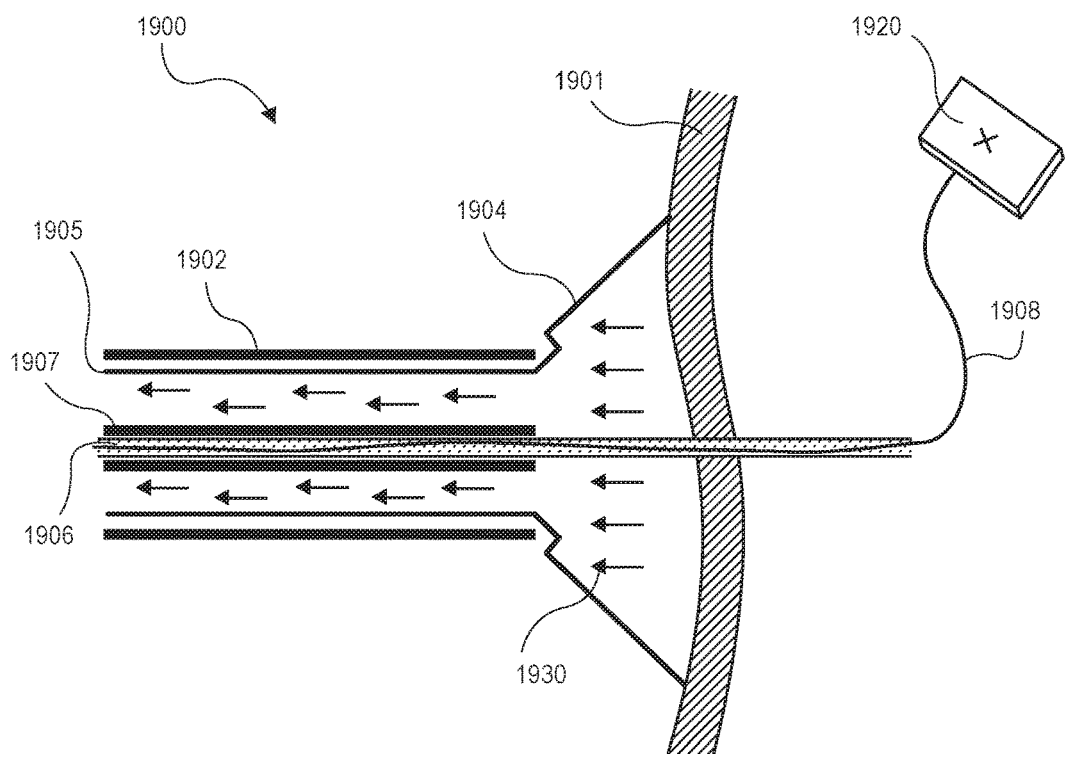

Referring to FIGS. 19A and 19B, in one exemplary embodiment, the leaflet 1901 is in a temporarily fixed position, so that the needle 1906 can be brought into stable contact with the leaflet 1901 at the desired location on the leaflet. A wide variety of different devices can be used to hold the leaflet 1901. In an exemplary embodiment, a catheter 1902 with a collapsible suction cup 1904 at the distal end thereof is used to temporarily engage or hold at least a portion of the valve leaflet in a fixed position. The suction catheter 1904 can be used in any of the procedures and devices described herein. Once engaged or held, the leaflet can be punctured with a needle 1906, and a pledget 1920 with a line attached thereto can be deployed, using the methods disclosed herein.

FIGS. 19A and 19B illustrate an exemplary embodiment of a side cross section of a distal end of a delivery device 1900 while engaged with an atrioventricular heart valve leaflet 1901, for example, a mitral valve leaflet. The delivery device includes an elongate outer catheter 1902 that is deployable using a minimally invasive procedure to the heart valve leaflet. For example, the catheter can be deployed transapically or transseptally. A suction or vacuum catheter 1905 extends through the outer catheter 1902. A proximal end of a lumen of the suction catheter 1905 is fluidly coupled to a source of suction or vacuum (not illustrated). In one exemplary embodiment, the suction catheter 1905 is filled with a liquid, such as water, blood, or a saline solution. In one example, the suction catheter 1905 contains substantially no air when introduced. A suction cup 1904, such as a frustoconical suction cup, extends from a distal end of the suction catheter 1905. In the illustrated embodiment, the suction cup 1904 is collapsible and is extendable out of and retractable into the outer catheter 1902. Some embodiments of the deployed suction cup 1904 are at least partially axially collapsible when engaging tissue under suction (suction indicated by arrows 1930). FIG. 19B shows the delivery device 1900 having the deployed suction cup 1904 partially axially collapsed. The device also includes a needle catheter 1907 through which a slidable needle 1906 advances through or retracts from the leaflet 1901. In the illustrated embodiment, the needle catheter 1907 is generally coaxial with the outer catheter 1902, but is offset in other embodiments. A line extends through and out of a lumen in the slidable needle 1906. Other embodiments include at least one additional slidable needle, which permits placing multiple lines in a single operation, or selecting the needle at the more desired position for placing the artificial chord. Some embodiments of the delivery device include an imaging element, for example, an ultrasound transducer, the use of which will be apparent from the following discussion. The needle catheter 1907 can also fit a hypotube needle such as the exemplary embodiments disclosed herein in FIGS. 5-7, 8A-8B, which can contain one or more pledgets to be dispensed therefrom.

In an embodiment of a method for placing an artificial chord 1908 using the delivery device of FIGS. 19A and 19B as an example, a distal end portion of the outer catheter 1902 is positioned in proximity of a location on a leaflet 1901 needing an artificial chord, for example, under echo or fluoroscopic guidance. The suction cup 1904 is extended from the distal end of the outer catheter 1902, either in close proximity to or at least partially contacting the leaflet 1901. Suction or vacuum is then applied through the lumen of the suction catheter 1905, which pulls the leaflet 1901 against an opening or distal end of the suction cup 1904, thereby capturing and holding the leaflet 1901. Capture can be confirmed by imaging, for example, echo or fluoroscopy. If the leaflet is not captured at the desired location, the suction is released or reduced sufficiently to permit repositioning the suction cup 1904. Once properly positioned, the slidable needle 1906 is then advanced from the needle catheter 1907 and through the leaflet 1901. The slidable needle can be a hypotube needle in accordance with an exemplary embodiment, as disclosed herein. An end of the line 1908 extending from the needle 1906 is secured to the leaflet 1901, for example, using a knot or clip (see, for example, U.S. Patent Application Publication No. 2014/0114404 A1, which is incorporated herein by reference in its entirety), or using a pledget fixedly or slidably attached to the line. The length of the line is adjusted to correct leaflet motion, for example, by observing reduced regurgitation by Doppler ultrasound imaging. Another end of the line 1908 is then secured to another structure, for example, a ventricular wall, ventricular septum, and/or papillary muscle, to complete the artificial chord. The device and any excess line is removed.

In some embodiments, the line 1908 is similar to, and is deployed analogously to the artificial chord described in U.S. Pat. No. 7,635,386, the entire content of which is incorporated by reference in its entirety.

Embodiments of the disclosed system, device, and method include the ability to reposition the suction cup 1904 until the desired positioning is achieved. Another advantage is that the leaflet is captured and immobilized relative to the line 1908 and needle 1906, which permits a more precise placement of the artificial chord 1908 compared with methods in which the leaflet is moving relative to the line 1908 at some time during deployment.

Figure 20:
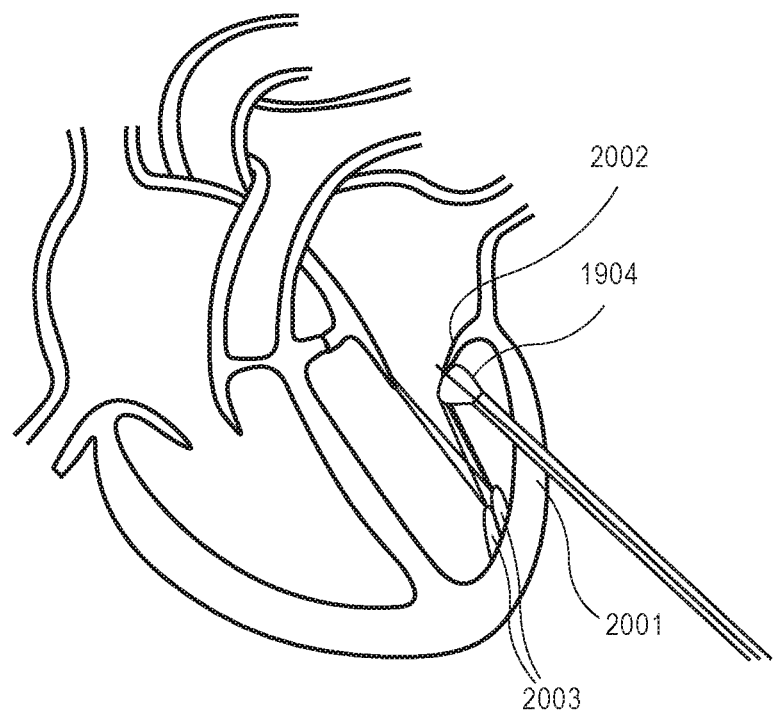
FIG. 20 illustrates an embodiment of a transventricular wall approach for the artificial chord delivery device shown in FIGS. 19A and 19B.

The suction catheter 1905 and suction cup 1904 can be used to secure lines to valve tissue in any of the ways described herein. FIG. 20 illustrates an embodiment of a method for placing an artificial chord on a posterior leaflet of a mitral valve using the delivery device of FIGS. 19A and 19B. In the illustrated embodiment, the suction cup 1904 of the device accesses a mitral posterior valve leaflet 2002 through an opening in a ventricular wall 2001. In other embodiments, the leaflet is an anterior leaflet of the mitral valve, or one of the leaflets of the tricuspid valve. In FIG. 20, the delivery device penetrates the ventricular wall above the papillary muscles 2003. In other embodiments, the delivery device penetrates the ventricular wall proximate a papillary muscle, through a papillary muscle, through the intraventricular septum, or at or near the apex of the heart. In other embodiments, the device can be used to approximate the leaflets together, as accomplished by the Alfieri stitch.

Figure 21:
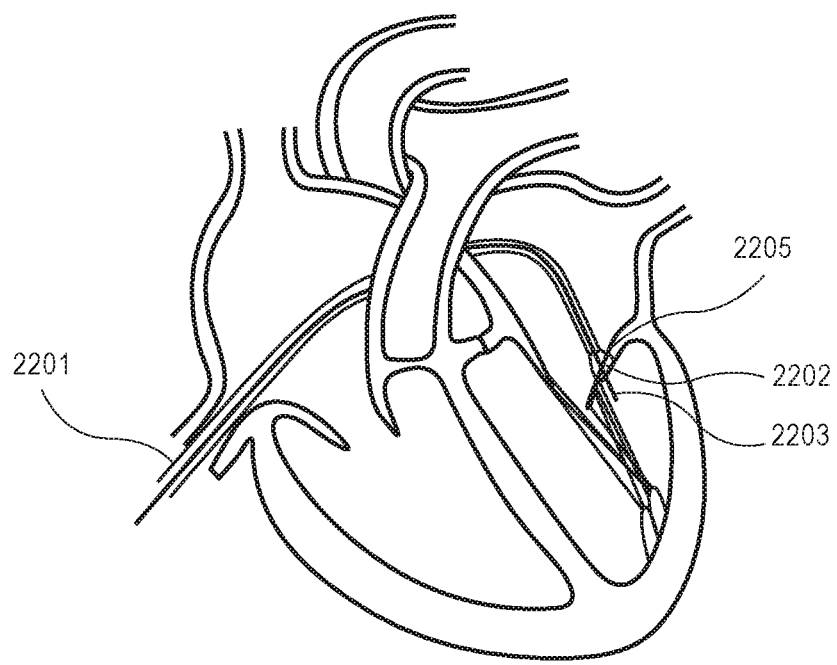
FIG. 21 illustrates an embodiment of a transseptal approach for the artificial chord delivery device shown in FIGS. 19A and 19B.

FIG. 21 illustrates another embodiment of a method for accessing a mitral valve leaflet by a transseptal approach from the right atrium to the left atrium. This approach can be used to tie the mitral valve leaflets together in generally the same manner as described with respect to FIGS. 17A-17B and 18. However, the pledgets or other type of anchor are disposed on the ventricular side of the leaflets. Those skilled in the art will understand that a similar approach is useful in accessing the tricuspid valve leaflet where the delivery device accesses the right atrium through, for example, one of the superior or inferior vena cava. A variety of different procedures can be performed by accessing the leaflets of the mitral valve or the tricuspid valve from the atrial side as illustrated by FIG. 21. The suction cup 2202 can be used in any procedure to hold heart tissue, such as a valve leaflet 2205. A needle 2203 or other device can penetrate the heart tissue from the atrial side while the tissue is held by the suction cup 2202.

Figure 22:
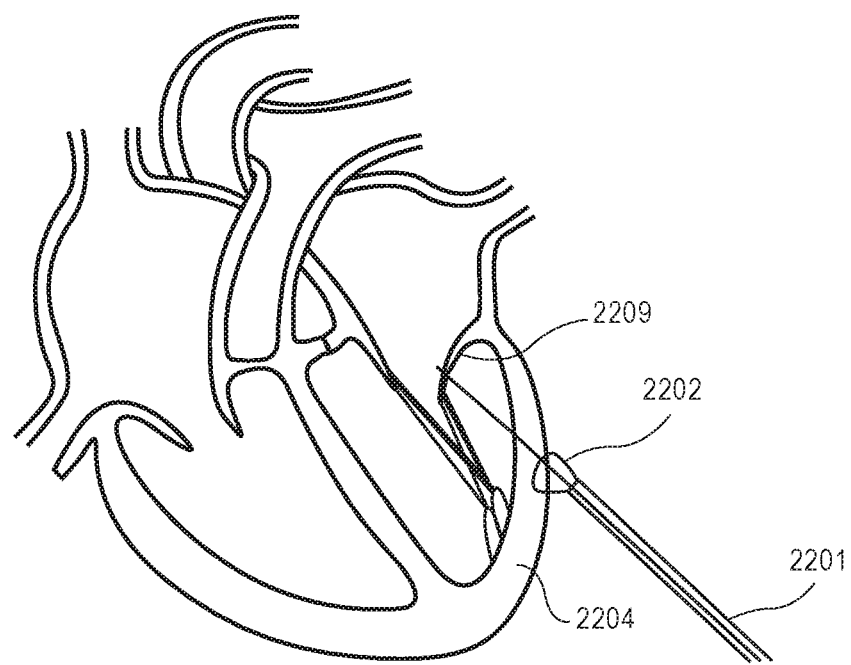
FIG. 22 illustrates an alternative transventricular wall approach for the artificial chord delivery device shown in FIGS. 19A and 19B.

In the example illustrated by FIG. 22, the distal end of the outer catheter 2201 and the suction cup 2202 captures or engages tissue other than a leaflet, for example, to stabilize the delivery device. For example, in FIG. 22, the suction cup 2202 at the distal end of the outer catheter 2201 engages the left ventricular wall 2204 while the needle (not shown) is deploying a line to the posterior leaflet 2209 of the mitral valve. In other embodiments, the suction cup 2202 engages other tissue, for example, a ventricular wall at or near the apex, an atrial wall, the intraventricular septum, or the interatrial septum, which permits accessing any of the mitral or tricuspid valve leaflets for placing one or more artificial chords.

Figure 23:
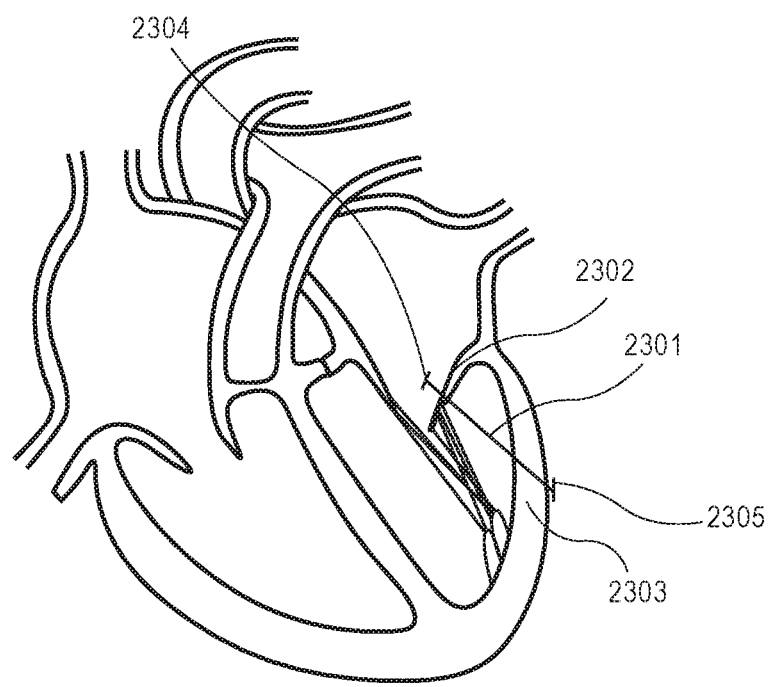
FIG. 23 illustrates an example of an artificial chord placed using the artificial chord delivery device.

FIG. 23 illustrates an embodiment of an artificial chord 2301 delivered according to any of the approaches illustrated in FIGS. 20-22. In the illustrated embodiment, a first end of the artificial chord 2301 is secured to the anterior mitral valve leaflet 2302 and a second end is anchored at an outside surface of the ventricular wall 2303. Other embodiments are anchored at another location, for example, within the myocardium, to a papillary muscle, to the intraventricular septum, or to a natural chord or artificial chord, such as a line. Suitable anchors 2304, 2305 include pledgets, knots, clips, discs, hooks, barbs, and/or adhesives.

The methods and devices described herein are not limited to use within the mitral valve of the heart. They can be used in any heart valve or other valve tissue in the body, such as the tricuspid valve, in which leaflets are to be repaired, coapted, or otherwise repositioned.

Further, although some of the embodiments have been described herein in the context of a particular implementation in a particular environment for a particular purpose, those of ordinary skill in the art should recognize that its usefulness is not limited thereto and that the various embodiments can be beneficially implemented in any number of environments for any number of purposes. Accordingly, the claims set forth below should be construed in view of the full breadth and spirit of the embodiments as disclosed herein. While the foregoing description includes many details and specificities, it is to be understood that these have been included for purposes of explanation only, and are not to be interpreted as limitations of the various embodiments. Modifications to the embodiments described above can be made without departing from the spirit and scope of this description.

What is claimed is:

1. A method comprising the steps of:
   introducing into a ventricle of a heart proximate to a heart valve leaflet a catheter with a suction cup at a distal end, and a needle positioned within the catheter, wherein the needle comprises an opening;
   contacting a ventricular side of the heart valve leaflet with a distal end of the suction cup;
   partially axially collapsing the suction cup while engaging the ventricular side of the heart valve leaflet and applying a negative pressure through the suction cup to the ventricular side of the heart valve leaflet;
   advancing the needle out of the suction cup to pierce the heart valve leaflet while applying the negative pressure to the ventricular side of the heart valve leaflet through the suction cup and partially axially collapsing the suction cup, wherein the heart valve leaflet is pierced by passing the portion of the needle with the opening through the heart valve leaflet;
   deploying through the opening of the needle onto the atrial side of the heart valve leaflet a distal end of a line;
   withdrawing the needle from the heart valve leaflet into the catheter such that a portion of the distal end of the line remains on the atrial side of the heart valve leaflet; and
   releasing the negative pressure to remove the suction cup from the ventricular side of the heart valve leaflet.

2. The method of claim 1, wherein a first pledget is disposed at the distal end of the line, the method further comprising contacting the ventricular side of the heart valve leaflet with the suction cup and applying negative pressure a second time;
   extending the needle out of the distal end of the suction cup;
   piercing the heart valve leaflet with the line a second time while the negative pressure is applied the second time;
   deploying through the opening of the needle onto the atrial side of the heart valve leaflet a second pledget, wherein the second pledget is slidably attached to the line;
   withdrawing the needle from the heart valve such that the second pledget remains on the atrial side of the heart valve leaflet; and
   removing the negative pressure and the suction cup from the ventricular side of the heart valve leaflet.

3. The method of claim 2, further comprising contacting the ventricular side of the heart valve leaflet with the suction cup and applying negative pressure a third time;
   extending the needle out of the distal end of the suction cup;
   piercing the heart valve leaflet with the needle a third time while the negative pressure is applied the third time;
   deploying through the opening of the needle onto the atrial side of the heart valve leaflet a third pledget, wherein the third pledget is slidably attached to the line; and
   withdrawing the needle from the heart valve such that the third pledget remains on the atrial side of the heart valve leaflet.

4. The method of claim 1, wherein a first pledget is disposed at the distal end of the line, the method further comprising withdrawing the needle from the ventricle of the heart;
   anchoring the line to the heart;
   reintroducing the needle into the ventricle of the heart proximate to one of the heart valve leaflet or a second heart valve leaflet;
   applying a negative pressure to the heart valve leaflet or the second heart valve leaflet through the suction cup;
   extending the needle out of the distal end of the suction cup;
   contacting a ventricular side of the heart valve leaflet or the second heart valve leaflet with the needle;
   piercing the heart valve leaflet or the second heart valve leaflet with the needle while the negative pressure is applied;
   deploying through the opening of the needle onto the atrial side of the heart valve leaflet or the second heart valve leaflet a second pledget, wherein the second pledget is slidably attached to the line; and
   withdrawing the needle from the heart valve leaflet or the second heart valve leaflet such that the second pledget and a portion of the distal end of the line remains on the atrial side of the heart valve leaflet or the second heart valve leaflet.

5. The method of claim 4, further comprising contacting the ventricular side of the heart valve leaflet or the second heart valve leaflet with the needle a second time;
   applying a negative pressure to the heart valve leaflet or the second heart valve leaflet through the suction cup;
   extending the needle out of the distal end of the suction cup;
   deploying through the opening of the needle onto the atrial side of the heart valve leaflet or the second heart valve leaflet a third pledget, wherein the third pledget is slidably attached to the line; and
   withdrawing the needle from the heart valve such that the third pledget remains on the atrial side of the heart valve leaflet or the second heart valve leaflet.

6. The method of claim 5, further comprising the step of deploying a connector attached to the line and stored in the needle after the needle is withdrawn from the heart valve leaflet or the second heart valve leaflet.

7. The method of claim 1, further comprising fixing a proximal portion of the line to the heart.

* * * * *